(12) United States Patent
Bigge et al.

(10) Patent No.: US 6,703,391 B2
(45) Date of Patent: *Mar. 9, 2004

(54) QUINOXALINEDIONE DERIVATIVES, THEIR PREPARATION AND USE

(75) Inventors: Christopher Franklin Bigge, Ann Arbor, MI (US); Thomas Charles Malone, Canton, MI (US); Frank Watjen, Copenhagen (DK)

(73) Assignee: Neurosearch A/S, Ballerup (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/443,507

(22) Filed: May 18, 1995

(65) Prior Publication Data

US 2003/0114422 A1 Jun. 19, 2003

Related U.S. Application Data

(60) Division of application No. 08/375,059, filed on Jan. 19, 1995, now abandoned, which is a continuation of application No. 08/124,770, filed on Sep. 24, 1993, now abandoned, which is a continuation-in-part of application No. 08/034,332, filed on Mar. 22, 1993, now abandoned, which is a continuation-in-part of application No. 07/960,157, filed on Oct. 13, 1992, now abandoned.

(51) Int. Cl.⁷ .................. C07D 487/04; C07D 217/04; C07D 217/02; A61K 31/4985
(52) U.S. Cl. .................. 514/250; 544/345; 544/244; 546/139; 546/143; 546/150; 546/166; 548/482
(58) Field of Search .................. 544/345, 244; 514/250, 81

(56) References Cited

U.S. PATENT DOCUMENTS

| | | | |
|---|---|---|---|
| 5,057,516 A | 10/1991 | Jacobsen et al. | 514/250 |
| 5,075,306 A | 12/1991 | Jacobsen et al. | 514/250 |
| 5,079,250 A | 1/1992 | Jacobsen et al. | 514/250 |
| 5,182,279 A | 1/1993 | Jorgensen et al. | 514/250 |
| 6,197,771 B1 * | 3/2001 | Bigge et al. | 514/250 |

FOREIGN PATENT DOCUMENTS

| | | |
|---|---|---|
| EP | 0283959 | 9/1988 |
| EP | 0374534 | 6/1990 |
| EP | 0529636 A1 | 3/1993 |
| WO | 9207847 | 5/1992 |

OTHER PUBLICATIONS

Jensen, Acta Neurol Scand 85: 187 (1992).*
Frandsen, J. Neurochem. 5, 1821 (1990).*
Judge, Neurosci. Letters 133, 291–294 (1991).*
Gill, Brain Research 580, 35 (1992).*
Schielke, Stroke 30: 1472–1476, 1477 (1999).*
Koh, J. Neurosci. 10(2) 693 (1990).*

(List continued on next page.)

Primary Examiner—Mark L. Berch
(74) Attorney, Agent, or Firm—Birch, Stewart, Kolasch & Birch, LLP

(57) ABSTRACT

A compound having the formula

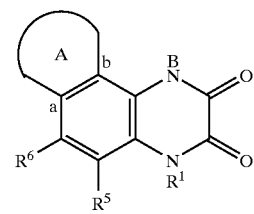

or a pharmaceutically acceptable salt thereof wherein
R is hydrogen or hydroxy;
$R^1$ is hydrogen,
  alkyl,
  arylalkyl,
  $(CH_2)_nOH$, or
  $(CH_2)_nNR^7R^8$;
$R^5$ and $R^6$ are each independently
  hydrogen,
  halogen,
  $NO_2$,
  CN,
  $CF_3$,
  $SO_2NR^7R^8$,
  $PO_3R^9R^{10}$,
  alkyl,
  alkenyl,
  alkynyl,
  $(CH_2)_nCONR^7R^8$,
  $(CH_2)_nCO_2R^{10}$,
  $NHCOR^{11}$,
A is a ring formed by the following:
  a-$NR^{12}$—$CHR^{13}$—$CHR^{14}$-b,
  a-$CHR^{13}$—$CHR^{14}$—$NR^{12}$-b,
  a-$CHR^{13}$—$NR^{12}$—$CHR^{14}$-b,
  a-$CHR^{14}$—$CH_2$—$NR^{12}$—$CHR^{13}$-b,
  a-$CHR^{13}$—$NR^{12}$—$CH_2$—$CHR^{14}$-b,
  a-$CH_2$—$CH_2$—$CHR^{13}$—$NR^{12}$-b,
  a-$NR^{12}$—$CHR^{13}$—$CHR^{12}$—$CH_2$—$CH_2$-b,
  a-$CH_2$—$CH_2$—$NR^{12}$—$CH_2$—$CH_2$-b,
  a-$CH_2$—$CH_2$—$CH_2NR^{12}$—$CH_2$-b,
  a-$CH_2$—$NR^{12}$—$CH_2$—$CH_2$-b
  a-$CH_2$—$CH_2$—$CH_2$—$CH_2$—$NR^{12}$-b,
  a-$NR^{12}$—$CH_2$—$CH_2$—$CH_2$—$CH_2$-b, The compounds are useful in the treatment of disorders responsive to the blockade of glutamic and aspartic acid receptors.

4 Claims, No Drawings

OTHER PUBLICATIONS

Honore, Neurosci. Letters 521, 27–32 (1985).*
Bigge, J. Med. Chem. 38, 3720 (1995).*
M. Rey, et al., *Chem Abstracts*, Vol 105, No. 19, 1986, Abstract No. 172255q, p. 727.
Krall, et al. Epilepsia 19, 409 (1978).
Sheardown, M.J. et al. *Science*, Vol 247, 1990, 571–574.
Derwent Abstract of WO–92/07847 (1992).
Sheardown et al., Science, vol. 247 (1990) pp. 571–574.
Meldrum, Epilepsy Research, vol. 12 (1992) pp. 189–196.
Smith et al., European Journal of Pharmacology, vol. 201 (1991) pp. 179–183.
Meldrum, Current Opinion in Neurology and Neurosurgery, vol. 5, No. 4, (1992) pp. 508–513.

* cited by examiner

QUINOXALINEDIONE DERIVATIVES, THEIR PREPARATION AND USE

CROSS REFERENCE

This is a divisional of U.S. application Ser. No. 08/375,059 filed Jan. 19, 1995, now ABN, which is a continuation of U.S. application Ser. No. 08/124,770 filed Sep. 24, 1993, now abandoned, which is a continuation-in-part of U.S. application Ser. No. 08/034,332 filed Mar. 22, 1993, now abandoned, which is a continuation-in-part of U.S. application Ser. No. 07/960,157 filed Oct. 13, 1992, now abandoned.

OBJECT OF THE INVENTION

It is an object of the present invention to provide novel quinoxaline dione compounds which are useful in the treatment of diseases in mammals, including a human, and especially in the treatment of diseases which can be treated by antagonizing an excitatory amino acid of such mammals.

Another object of the present invention is to provide a method of treating diseases in mammals, including a human, responsive to the blockade of glutamic and aspartic acid receptors which comprises administering to a mammal in need thereof a compound of the invention.

A third object of the present invention is to provide novel pharmaceutical compositions for the treatment of diseases in mammals, including a human, responsive to the blockade of glutamic and aspartic acid receptors.

BACKGROUND OF THE INVENTION

Excessive excitation by neurotransmitters can cause the degeneration and death of neurons. It is believed that this degeneration is in part mediated by the excitotoxic actions of the excitatory amino acids (EAA) glutamate and aspartate at the N-methyl-D-aspartate (NMDA), the α-amino-3-hydroxy-5-methyl-4-isoxazole propionic acid (AMPA) receptor, and the kainate receptor. This excitotoxic action is responsible for the loss of neurons in cerebrovascular disorders such as cerebral ischemia or cerebral infarction resulting from a range of conditions, such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma, as well as lathyrism, Alzheimer's, and Huntington's diseases.

The compounds of the present invention may also be useful in the treatment of schizophrenia, Parkinsonism, epilepsy, anxiety, pain, and drug addiction.

SUMMARY OF THE INVENTION

The invention then, inter alia, comprises the following, alone or in combination:
A compound having the formula

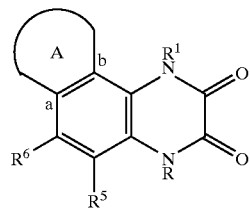

or a pharmaceutically acceptable salt thereof wherein

R is hydrogen or hydroxy;
$R^1$ is hydrogen,
  alkyl,
  arylalkyl,
  $(CH_2)_nOH$, or
  $(CH_2)_nNR^7R^8$;
$R^5$ and $R^6$ are each independently
  hydrogen,
  halogen,
  $NO_2$,
  CN,
  $CF_3$,
  $SO_2NR^7R^8$,
  $PO_3R^9R^{10}$,
  alkyl,
  alkenyl,
  alkynyl,
  $(CH_2)_nCONR^7R^8$,
  $(CH_2)_nCO_2R^{10}$,
  $NHCOR^{11}$,
wherein $R^7$ and $R^8$ are each independently hydrogen or alkyl or together $R^7$ and $R^8$ form a ring of from three to seven atoms,
  $R^9$ is hydrogen or alkyl,
  $R^{10}$ is hydrogen or alkyl,
  $R^{11}$ is hydrogen or alkyl, and
  n is an integer of from zero to four;
A is a ring of five to seven atoms fused with the benzo ring at the positions marked a and b, and formed by the following bivalent radicals:
  a-$NR^{12}$—$CHR^{13}$—$CHR^{14}$-b,
  a-$CHR^{13}$—$CHR^{14}$—$NR^{12}$-b,
  a-$CHR^{13}$—$NR^{12}$—$CHR^{14}$-b,
  a-$CHR^{14}$—$CH_2$—$NR^{12}$—$CHR^{13}$-b,
  a-$CHR^{13}$—$NR^{12}$—$CH_2$—$CHR^{14}$-b,
  a-$CH_2$—$CH_2$—$CHR^{13}$—$NR^{12}$-b,
  a-$NR^{12}$—$CHR^{13}$—$CH_2$—$CH_2$-b,
  a-$CH_2$—$CH_2$—$NR^{12}$—$CH_2$—$CH_2$-b,
  a-$CH_2$—$CH_2CH_2$—$NR^{12}$—$CH_2$-b,
  a-$CH_2$ $NR^{12}$—$CH_2$—$CH_2$—$CH_2$-b,
  a-$CH_2$—$CH_2$—$CH_2$—$CH_2$—$NR^{12}$-b,
  a-$NR^{12}$—$CH_2$—$CH_2$—$CH_2$—$CH_2$-b,
wherein
  $R^{12}$ is hydrogen, $CH_2CH_2OH$, or alkyl, and $R^{13}$ and $R^{14}$ are each independently hydrogen, CN, $CONH_2$, $CH_2NH_2$, $CH_2OH$, alkyl, arylalkyl, alkenyl, or $CO_2R^{15}$ wherein $R^{15}$ is hydrogen or alkyl;
and a compound as above having the formula

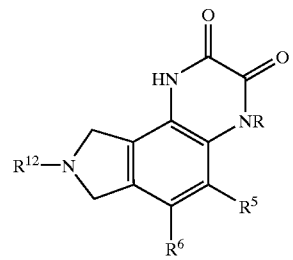

wherein R, $R^{12}$, $R^5$, and $R^6$ have the meanings set forth above;

and a compound as above having the formula

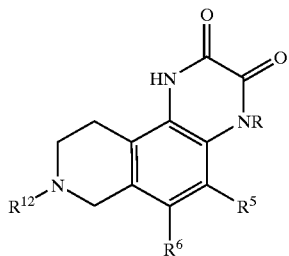

wherein R, $R^{12}$, $R^5$, and $R^6$ have the meanings set forth above;
and a compound as above having the formula

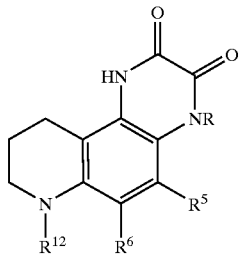

wherein R, $R^{12}$, $R^5$, and $R^6$ have the meanings set forth above;
and a compound as above having the formula

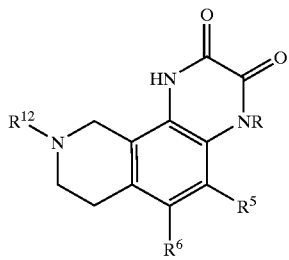

wherein R, $R^{12}$, $R^5$, and $R^6$ have the meanings set forth above;
and a compound as above having the formula

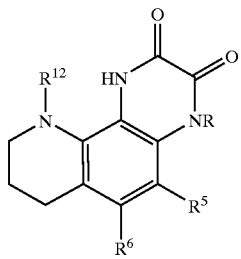

wherein R, $R^{12}$, $R^5$, and $R^6$ have the meanings set forth above;
and further a compound as any above wherein $R^5$ and $R^6$ independently are
  hydrogen,
  halogen,
  $NO_2$,
  CN,
  $SO_2NR^7R^8$ wherein $R^7$ and $R^8$ independently are hydrogen or $C_{1-3}$-alkyl which may be straight or branched or cyclic, and wherein $R^{12}$ is $C_{1-3}$-alkyl which may be straight or branched or cyclic;
and a compound having the formula

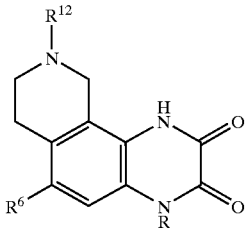

wherein $R^{12}$ is hydrogen, methyl, or ethyl and $R^6$ is $NO_2$, $SO_2NMe_2$,

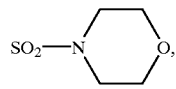

or

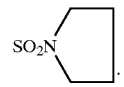

and a compound having the formula

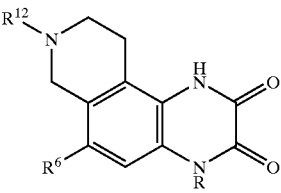

wherein $R^{12}$ is hydrogen, methyl, or ethyl and $R^6$ is $NO_2$, $SO_2NMe_2$,

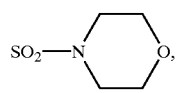

or

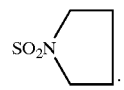

and further method of treating disorders of a mammal, including a human, responsive to the blockade of glutamic and aspartic acid receptors, which comprises administering to a patient in need thereof an effective amount of a compound as any above in unit dosage form;
and a method as above wherein cerebrovascular disorders are treated;
and further a pharmaceutical composition comprising a therapeutically effective amount of a compound as any above together with a pharmaceutically acceptable carrier.

Examples of pharmaceutically acceptable addition salts include inorganic and organic acid addition salts such as the hydrochloride, hydrobromide, phosphate, sulphate, citrate, lactate, tartrate, maleate, fumarate, mandelate, oxalate, and the acetate.

Halogen is fluorine, chlorine, bromine, or iodine; fluorine, chlorine, and bromine are preferred groups.

Alkyl means a straight chained or branched chain of from one to six carbon atoms or cyclic alkyl of from three to seven carbon atoms including, but not limited to methyl, ethyl, propyl, isopropyl, butyl, isobutyl, t-butyl, pentyl, hexyl, cyclopropyl, cyclobutyl, cyclopentyl, and cyclohexyl.

Alkenyl means a straight chained or branched chain alkenyl group of two to six carbon atoms or a cyclic alkenyl group of three to seven carbon atoms, for example, but not limited to ethylene, 1,2- or 2,3-propylene, 1,2-, 2,3-, or 3,4-butylene, cyclopentene, or cyclohexene.

Alkynyl means a straight chained or branched chain alkynyl group of two to six carbon atoms, for example, but not limited to ethynyl, 2,3-propynyl, 2,3- or 3,4-butynyl.

Aryl means a monocyclic or bicyclic carbocyclic aromatic ring system, for example, but not limited to phenyl, 2-naphthyl, or 1-naphthyl.

Arylalkyl means aryl as defined above and alkyl as defined above, for example, but not limited to benzyl, 2-phenylethyl, 3-phenylpropyl; a preferred group is benzyl.

Also included in the instant invention is a process for preparing a compound of formula (see Scheme I).

The process comprises (1) reacting a compound of Formula I (Scheme I) with a brominating agent, for example, bromine in trifluoroacetic acid, bromine in acetic acid or mixtures thereof, or reacting a compound of Formula I with a chlorinating agent, for example, sodium hypochlorite in hydrochloric acid to give a compound of Formula II

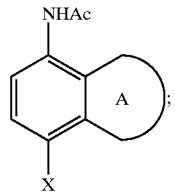

II wherein X is bromine or chlorine;

(2) treating a compound of Formula II above with fuming nitric acid in a solvent such as trifluoroacetic acid, acetic acid, or with mixtures thereof to give a compound of Formula III

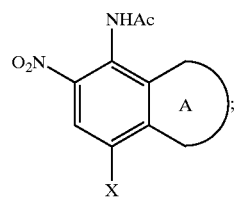

III (3) deprotecting a compound of Formula III with under acidic or basic conditions to provide a compound of Formula IV

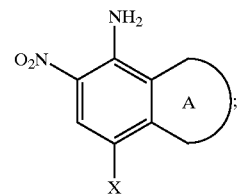

IV (4) hydrogenating a compound of Formula IV in a solvent to give a compound of Formula V

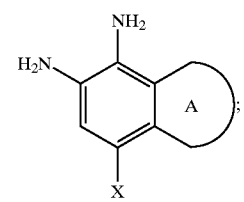

V wherein X may be hydrogen, bromine, or chlorine;

(5) reacting a compound of Formula V with oxalic acid in a solvent such as aqueous HCl or aqueous methanesulfonic acid or with diethyl oxylate to give a compound of Formula VI

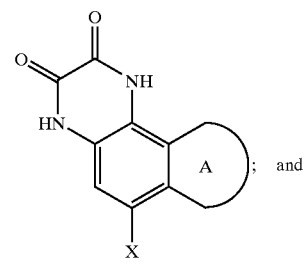

VI

; and (6) reacting a compound of Formula VI wherein X is hydrogen sequentially with chlorosulfonic acid neat or in a solvent followed by treatment with a primary or secondary amine to give a compound of Formula VII

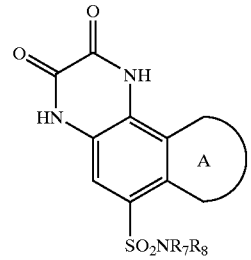

VII wherein $R_7$ and $R_8$ are as previously defined.

Also included in the invention is a process for the preparation of formula

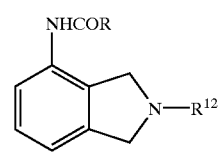

which comprises;

(1) reacting 3-nitrophthalic acid with a 1,3-dialkyl urea, neat or in a solvent to provide a compound of the formula

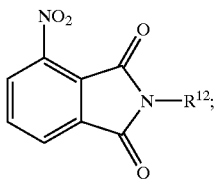

(2) hydrogenating a compound of the above formula in a solvent to give a compound of the formula

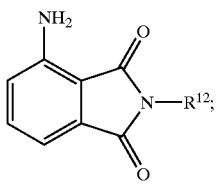

(3) reacting a compound of the above formula with a hydride reducing agent, for example, lithium aluminum hydride or the like in a solvent to give the compound of the formula

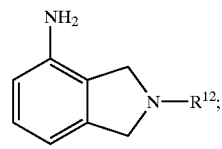

(4) reacting a compound of the above formula with an acid chloride or acid anhydride, for example, acetyl chloride, ethyloxalyl chloride, acetic anhydride, or the like in a solvent to give a compound of the formula

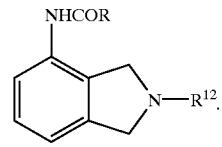

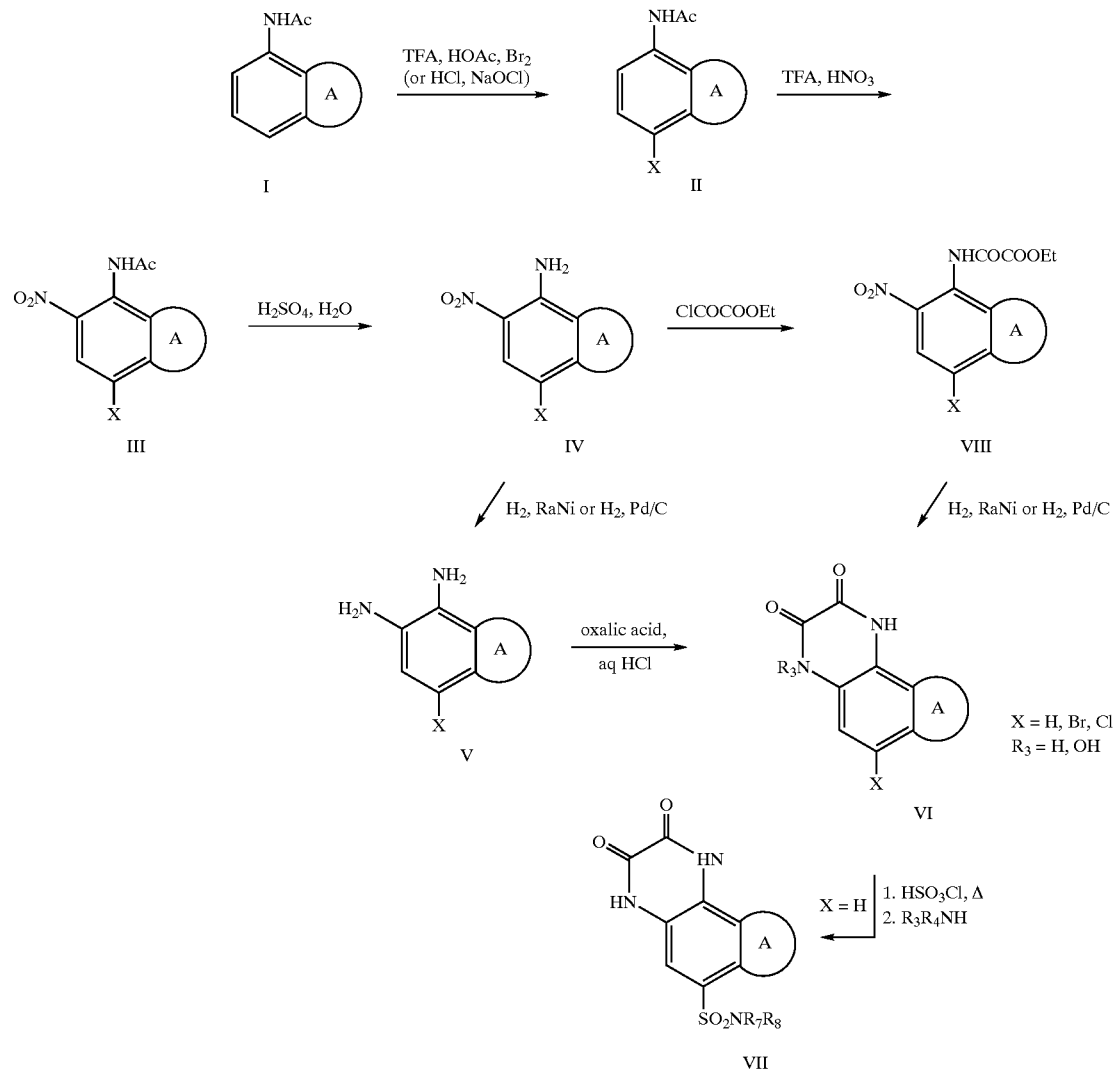

SCHEME I

Biological Activity

The compounds of the invention exhibit valuable biological properties because of their strong excitatory amino acid (EAA) antagonizing properties at the AMPA ((RS)-α-amino-3-hydroxy-5-methyl-4-isoxazole-propionic acid) binding site.

The compounds of the present invention exhibit binding affinity for the AMPA receptor as described by Honoré T, et al, *Neuroscience Letters* 1985;54:27–32 with $IC_{50}$ values of <100 μM in this assay. Values for selected compounds are found in Table I.

To functionally measure AMPA antagonist activity, the effects of the excitatory amino acid antagonists on AMPA-induced neuronal degeneration in primary cortical neuronal cultures were examined using techniques similar to those outlined by Koh, et al. (*J. Neurosci.* 1990;10:693–705). When using a 100 μM AMPA challenge, the claimed compounds generally had $IC_{50}$ values <30 μM.

Also, compounds of the present invention when administered TV or IP in the in vivo AMPA seizure test, as described below, inhibit the clonic seizures induced by AMPA.

AMPA-Induced Clonic Seizures

AMPA given ICV (intracerebroventricular) (15 μg/kg) to NMRI mice induces clonic seizures which should be inhibited by non-NMDA receptor antagonists.

Method

Test compound was given IV 5 minutes (or PO 30 minutes) before a 0.3 μg ICV administration of AMPA to ten female NMRI mice (weighing 24–26 g) per dose. The number of mice experiencing clonic seizures within the next 5 minutes was noted. An $ED_{50}$ value was calculated as the dose inhibiting 50% of the mice from having clonic seizures.

As a preliminary indicator of in vivo CNS activity, a maximal electroshock assay in CF-1 strain mice (20–25 g) is performed with corneal electrodes by conventional methods as described previously (Krall, et al., *Epilepsia* 1978;19:409–428). The claimed compounds generally demonstrated $ED_{50}$ values of <50 mg/kg.

TABLE I

Inhibition of [$^3$H] Ligand Binding to Cortical Membranes From Rat Brain

| Compound | Substituent (X, Y) | $IC_{50}$ (μM) [$^3$H] AMPA | [$^3$H] KA | [$^3$H] GLY |
|---|---|---|---|---|
| AMPA | | 0.036 | 30 | >100 |
| Kainic acid | | 8.2 | 0.013 | >100 |
| Glutamate | | 0.2 | 0.2 | — |
| Glycine | | 58 | >300 | 0.16 |
| NBQX | | 0.1 | 8 | >100 |
| Type A | | | | |
| Example | $CH_3$, H | 18 μM | | |
| | $CH_3$, Br | 0.57 μM | | |
| | $C_2H_5$, H | 41 μM | | |
| | $C_2H_5$, Br | 0.74 μM | | |
| Type B | $CH_3$, H | 8 | >30 | |
| | $CH_3$, Br | 2.4 | 41 | |
| | $C_2H_5$, H | 21 | >30 | |
| | $C_2H_5$, Br | 1.3 | 14 | |
| | $C_3H_7$, H | 18.5 | >30 | |
| Type C | H | 24 | 47 | |
| | $CH_3$ | 24 | *150 | |
| | $COCOOC_2H_5$ | | | |
| AMPA | | 0.036 | 30 | >100 |
| Kainic acid | | 8.2 | 0.013 | >100 |
| Glutamate | | 0.2 | 0.2 | — |
| Glycine | | 58 | >300 | 0.16 |
| NBQX | | 0.1 | 8 | >100 |
| Quinoxalinediones | | | | |
| Example | $CH_3$, Br, H | 1.1 | 12 | 3.3 |
| | $CH_3$, Br, OH | 0.94 | 13 | 3.3 |
| | $CH_3$, H, H | 3 | 56 | NT |
| | $CH_3$, H, OH | 0.38 | 17 | NT |
| | $CH_3$, Cl, H | 1.3 | 13 | NT |
| | $C(CH_3)_3$, Br, H | 1.6 | 30 | NT |
| | $CH_3$, $SO_2N(CH_3)_2$, H | 2.6 | NT | NT |
| | $CH_3$, $SO_2N$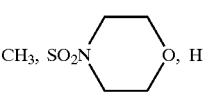O, H | 3.0 | NT | NT |
| | $CH_3$, $SO_2N$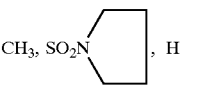, H | 3.4 | NT | NT |

NT = not tested

TABLE I-continued

Inhibition of [³H] Ligand Binding to Cortical Membranes From Rat Brain

| Compound | Substituent (X, Y) | IC₅₀ ($\mu$M) | | |
|---|---|---|---|---|
| | | [³H] AMPA | [³H] KA | [³H] GLY |

(Structures A, B, C shown)

Pharmaceutical Compositions

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing 10 mg of active ingredients or, more broadly, 0.1 to 100 mg per tablet, are accordingly suitable representative unit dosage forms.

Solid forms of pharmaceutical compositions for PO administration and injectable solutions are preferred.

Method of Treating

The compounds of this invention are extremely useful in the treatment of central nervous system disorders related to their biological activity. The compounds of this invention may accordingly be administered to a subject, including a human, in need of treatment, alleviation, or elimination of an indication associated with the biological activity of the compounds. This includes especially excitatory amino-acid-dependent psychosis, excitatory amino-acid-dependent anoxia, excitatory amino-acid-dependent ischemia, excitatory amino-acid-dependent Parkinsonism, excitatory amino-acid-dependent convulsions, and excitatory amino-acid-dependent migraine. Suitable dosage ranges are 0.1 to 1000 mg daily, 10 to 500 mg daily, and especially 30 to 100 mg daily, dependent as usual upon the exact mode of administration, form in which administered, the indication toward which the administration is directed, the subject involved, and the body weight of the subject involved, and further, the preference and experience of the physician or veterinarian in charge.

The following nonlimiting examples illustrate the present invention.

EXAMPLE 1

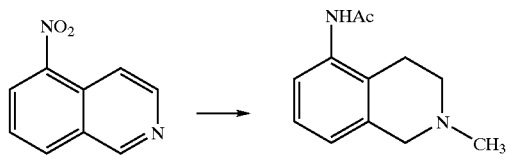

N-(1,2,3,4-tetrahydro-2-methyl-5-isoquinolinyl)-acetamide

A solution of 5-nitroisoquinoline (200 g, 1.15 mol) in 1000 mL of dimethylformamide was treated with dimethylsulfate (160 g, 1.27 mol), and the resulting solution was heated to 90° C. until no starting material remained. The reaction mixture was cooled and concentrated. The residue was dissolved in 1500 mL of methanol and hydrogenated over $PtO_2$ (1.0 g) at 52 psi for 15.5 hours. The reaction mixture was then concentrated and the residue dissolved in $CHCl_3$ (1000 mL) and washed with aqueous 1N NaOH solution (500 mL). The aqueous phase was extracted with an additional 3000 mL of chloroform, and the combined organic extracts were dried ($Na_2SO_4$) and concentrated to give an oil. The oil was treated with acetic anhydride (700 mL) and the resulting solution stirred at room temperature overnight. The reaction mixture was concentrated and the residue was dissolved in chloroform and washed with aqueous 1N NaOH solution. The organic phase was dried ($Na_2SO_4$) and concentrated. The residue was purified by chromatography (10:2 EtOAc:EtOH). The purified residue was recrystallized from EtOAc to give the product (60.6 g, 26%) as a white solid, mp=138–139° C.

EXAMPLE 2

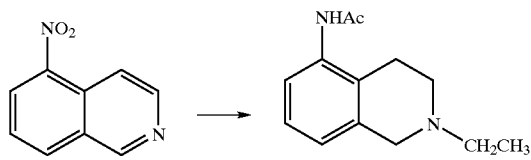

N-(2-ethyl-1,2,3,4-tetrahydro-5-isoquinolinyl) acetamide

A solution of 5-nitroisoquinoline (25 g, 0.144 mol) in 250 mL of EtOH was treated with iodoethane (26.9 g, 0.172 mol) and the resulting solution heated at reflux for 24 hours. The reaction mixture was cooled and the material which formed was collected and dried. The material obtained was converted to the title compound by the procedures described in Example 1. A white solid was obtained (4.42 g, 17%).

Analysis for ($C_{13}H_{18}N_2O$): Calc.: C, 71.53; H, 8.31; N, 12.83. Found: C, 71.43; H, 8.31; N, 12.91.

EXAMPLE 3

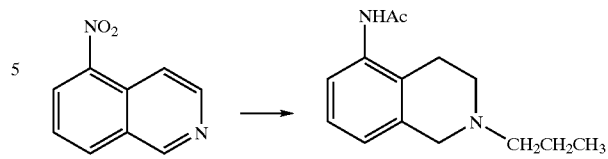

N-(1,2,3,4-tetrahydro-2-propyl-5-isoquinolinyl)-acetamide

A solution of 5-nitroisoquinoline (25 g, 0.144 mol) and iodopropane (36.7 g, 0.216 mol) in 500 mL of EtOH was converted to the title compound by the procedures described in Example 1. The crude title compound was purified by chromatography (silica gel, 95:5 EtOAc:EtOH). The purified product was recrystallized from $iPr_2O$/THF to give the title compound as a white solid (3.33 g, 18%), mp=123° C.

Analysis for ($C_{14}H_{20}N_2O$), Calc.: C, 72.38; H, 8.68; N, 12.06. Found: C, 72.38; H, 8.67; N, 12.14.

The filtrate was concentrated and the residue suspended in $iPr_2O$ and filtered to give a second crop of product (3.38 g, 19%).

EXAMPLE 4

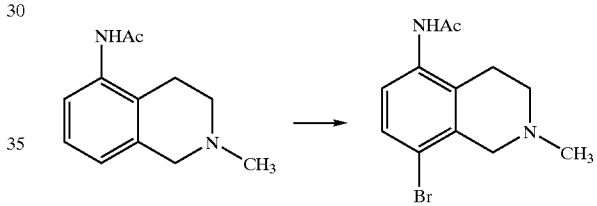

N-(8-bromo-1,2,3,4-t-tetrahydro-2-methyl-5-isoquinolinyl) acetamide

A solution of the product from Example 1 (22.6 g, 0.111 mol) in 500 mL of trifluoroacetic acid was treated dropwise with a 1 M solution of bromine in acetic acid (122 mL). The resulting solution was stirred at room temperature overnight during which time an orange suspension formed. The reaction was concentrated to an oil which was dissolved by the addition of EtOAc (200 mL) and saturated aqueous $NaHCO_3$ solution (100 mL). The aqueous phase was separated and extracted with additional EtOAc. The combined organic extracts were dried ($Na_2SO_4$) and concentrated. The residue was recrystallized from hot EtOAc to give the title compound as a white solid, mp=188–189° C.

Analysis for ($C_{12}H_{15}BrN_2O$): Calc.: C, 50.90; H, 5.34; N, 9.89. Found: C, 50.93; N, 5.01; N, 9.78.

EXAMPLE 5

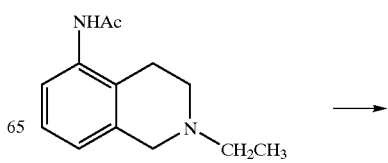

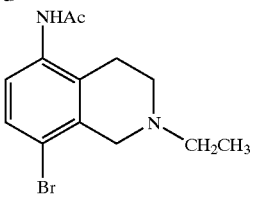

N-(8-bromo-2-ethyl-1,2,3,4-tetrahydro-5-isoquinolinyl)-acetamide

The product from Example 2 (3.65 g, 16.7 mmol) was converted to the title compound by the procedure described in Example 4. A white solid was obtained (2.64 g, 53%), mp=168–169° C.

Analysis for ($C_{13}H_{17}BrN_2O$): Calc.: C, 52.54; H, 5.77; N, 9.43. Found: C, 52.81; H, 5.23; N, 9.09.

EXAMPLE 6

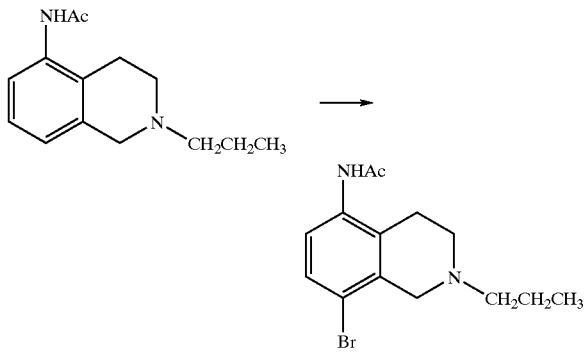

N-(8-bromo-1,2,3,4-tetrahydro-2-propyl-5-isoquinolinyl)acetamide

The product from Example 3 (6.33 g, 27.2 mmol) was converted to the title compound by the procedure described in Example 4. A white solid was obtained (6.17 g, 73%), mp=144–145° C.

Analysis for ($C_{14}H_{19}BrN_2O$): Calc.: C, 54.01; H, 6.15; N, 9.00. Found: C, 54.19; H, 6.06; N, 8.97.

EXAMPLE 7

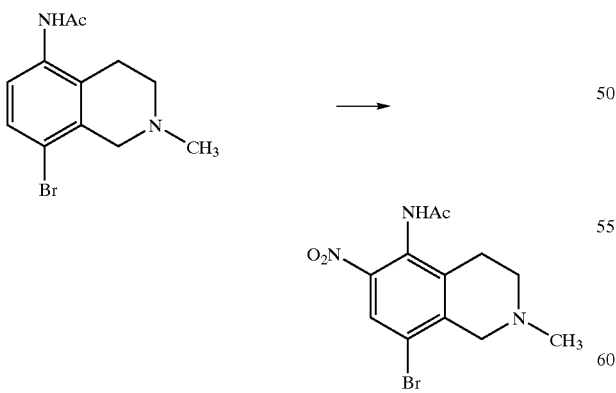

N-(8-bromo-1,2,3,4-tetrahydro-2-methyl-6-nitro-5-isoquinolinyl)acetamide

A solution of the product from Example 4 (19.8 g, 69.9 mmol) in 400 mL of trifluoroacetic acid was treated dropwise with fuming nitric acid (87 mL). The resulting solution was stirred at room temperature for 4 hours. The reaction mixture was concentrated and the residue dissolved by treatment with 3:1 EtOAc:THF and saturated aqueous NaHCO$_3$ solution. The organic phase was collected and the aqueous phase was extracted with additional 3:1 EtOAc:THF. The combined organic extracts were dried (Na$_2$SO$_4$) and concentrated. The residue was suspended in a THF/iPr$_2$O solution and the solid collected. Recrystallization from hot THF/iPr$_2$O provided the title compound as a beige solid (18.4 g, 80%), mp=190–192° C.

Analysis for ($C_{12}H_{14}BrN_3O_3$): Calc.: C, 43.79; H, 4.59; N, 12.77. Found: C, 43.98; H, 4.21; N, 12.84.

EXAMPLE 8

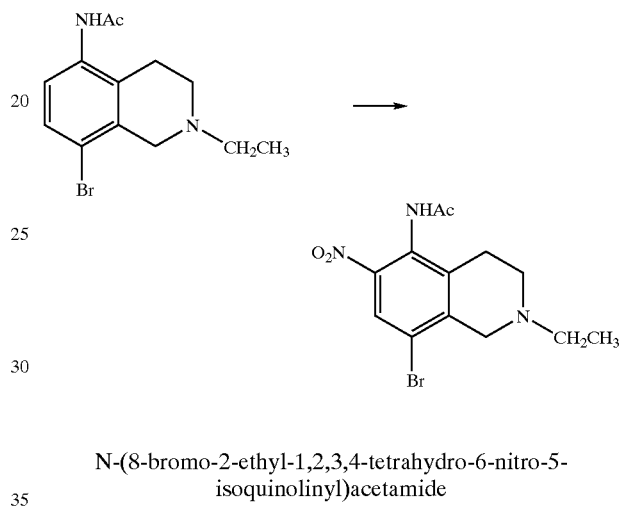

N-(8-bromo-2-ethyl-1,2,3,4-tetrahydro-6-nitro-5-isoquinolinyl)acetamide

The product from Example 5 (3.50 g, 11.8 mmol) was converted to the title compound by the procedure described in Example 7. A white solid was obtained (2.88 g, 71%), mp=168° C.

Analysis for ($C_{13}H_{16}BrN_3O_3$): Calc.: C, 45.63; H, 4.71; N. 12.28. Found: C, 45.84; H, 6.65; N, 12.06.

EXAMPLE 9

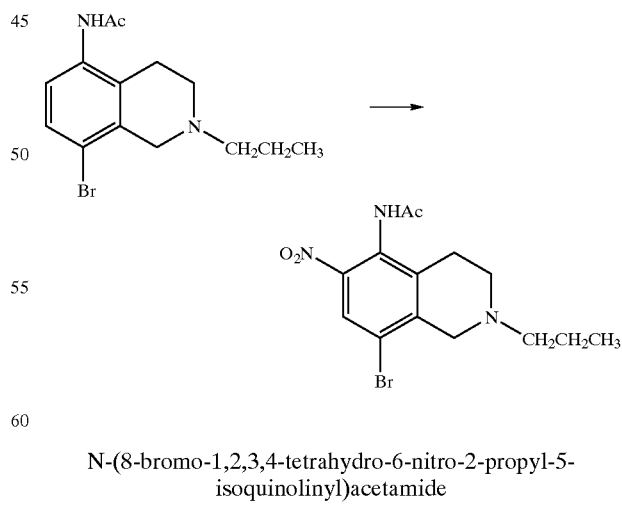

N-(8-bromo-1,2,3,4-tetrahydro-6-nitro-2-propyl-5-isoquinolinyl)acetamide

The product from Example 6 (5.50 g, 17.7 mmol) was converted to the title compound by the procedure described in Example 7. A white solid was obtained (4.41 g, 70%), mp=166–167° C.

Analysis for ($C_{14}H_{18}BrN_3O_3$): Calc.: C, 47.20; H, 5.09; N, 11.80. Found: C, 47.39; H. 5.00; N, 11.52.

EXAMPLE 10

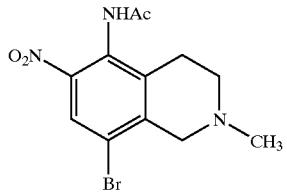
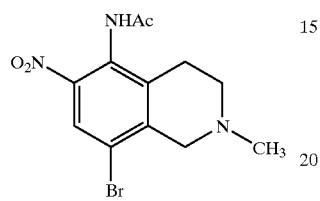

8-Bromo-1,2,3,4-tetrahydro-2-methyl-6-nitro-5-isoquinolinamine

A solution of the product from Example 7 (3.68 g, 11.2 mmol) and 80 mL of 3:2$H_2SO_4$:$H_2O$ was heated at 90° C. for 1 hour. The reaction mixture was cooled and poured onto ice, and the resulting solution was made basic with concentrated aqueous $NH_4OH$ solution. The solid that formed was collected by suction filtration and dried under vacuum to give the title compound as a yellow solid (3.17 g, 99%).

EXAMPLE 11

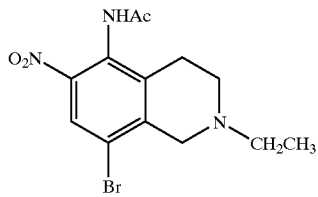
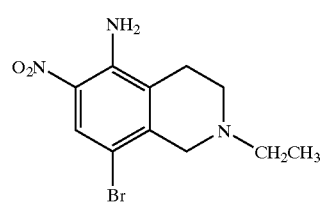

8-Bromo-2-ethyl-1,2,3,4-tetrahydro-6-nitro-5-isoquinolinamine

The product from Example 8 (2.50 g, 7.30 mmol) was converted to the title compound by the procedure described in Example 10. A yellow solid was obtained (2.05 g, 82%).

EXAMPLE 12

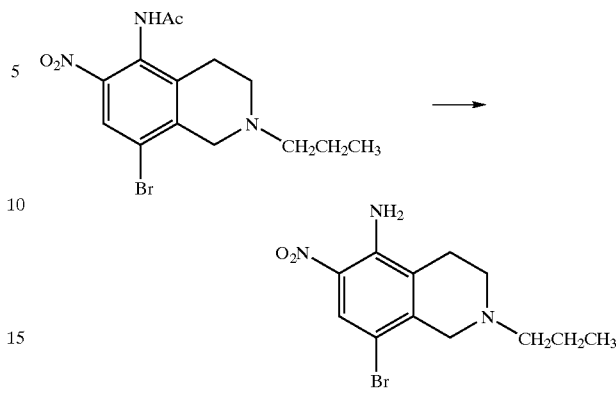

8-Bromo-1,2,3,4-tetrahydro-6-nitro-2-propyl-5-isoquinolinamine

The product from Example 9 (4.24 g, 11.9 mmol) was converted to the title compound by the procedure described in Example 10. A yellow solid was obtained (3.68 g, 98%).

EXAMPLE 13

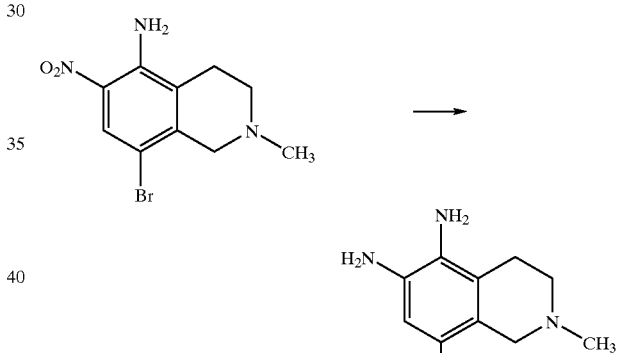

8-Bromo-1,2,3,4-tetrahydro-2-methyl-5,6-isoquinolinediamine

A solution of the product from Example 10 (0.78 g, 2.73 mmol) in 100 mL of THF was treated with Raney nickel (1.0 g) and hydrogenated for 1.5 hours at room temperature. The reaction mixture was filtered and concentrated to give the title compound as a tan solid (0.63 g, 90%).

EXAMPLE 14

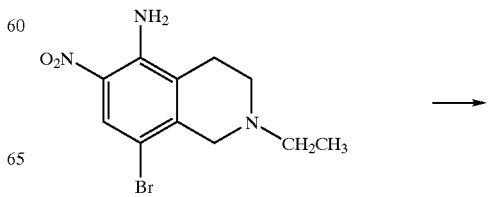

-continued

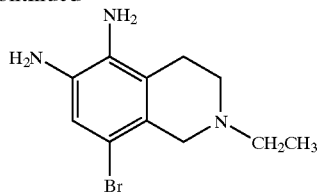

8-Bromo-2-ethyl-1,2,3,4-tetrahydro-5,6-isoquinolinediamine

The product from Example 11 (1.00 g, 3.33 mmol) was converted to the title compound by the procedure described in Example 13. An oil was obtained (0.88 g, 98%).

EXAMPLE 15

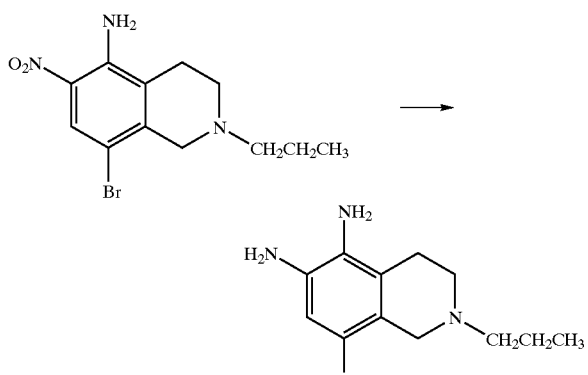

8-Bromo-1,2,3,4-tetrahydro-2-propyl-5,6-isoquinolinediamine

The product from Example 12 (0.98 g, 3.12 mmol) was converted to the title compound by the procedure described in Example 13. An oil was obtained (0.77 g, 87%).

EXAMPLE 16

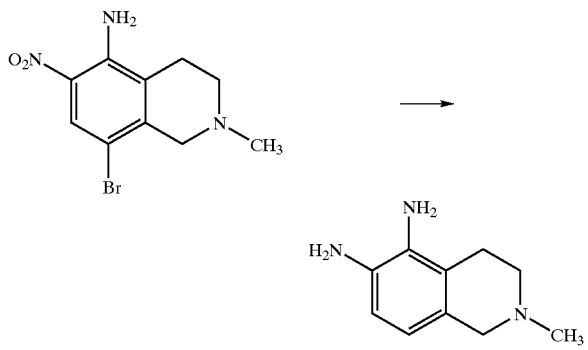

1,2,3,4-Tetrahydro-2-methyl-5,6-isoquinolinediamine

A solution of the product from Example 10 (1.50 g, 5.24 mmol) and 20% Pd on carbon (0.30 g) in 100 mL of MeOH was hydrogenated at room temperature and pressure for 24 hours. The reaction mixture was filtered and the filtrate concentrated. The residue was partitioned between CHCl$_3$ and saturated aqueous NaHCO$_3$ solution. The organic phase was separated and the aqueous phase was extracted with additional CHCl$_3$ and the combined organic extracts were dried (Na$_2$SO$_4$), filtered, and concentrated. The residue was filtered through a plug of silica gel eluting with 25% EtOH/EtOAc. The eluant was concentrated to give the title compound as an oil (0.45 g, 48%).

EXAMPLE 17

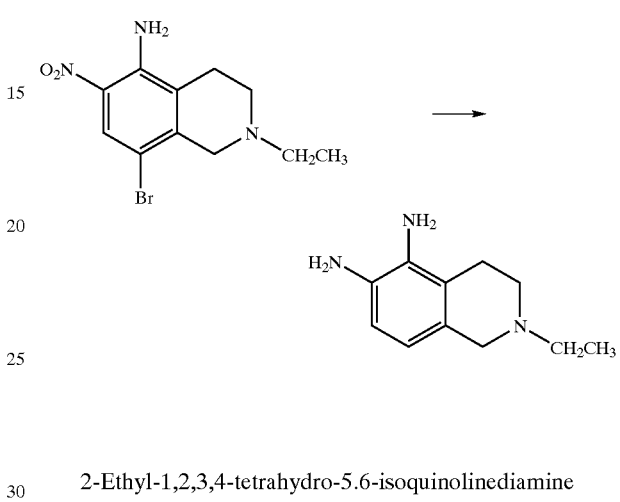

2-Ethyl-1,2,3,4-tetrahydro-5,6-isoquinolinediamine

The product from Example 11 (1.00 g, 3.33 mmol) was converted to the title compound by the procedure described in Example 16. An oil was obtained (0.70 g). This material was used without further purification.

EXAMPLE 18

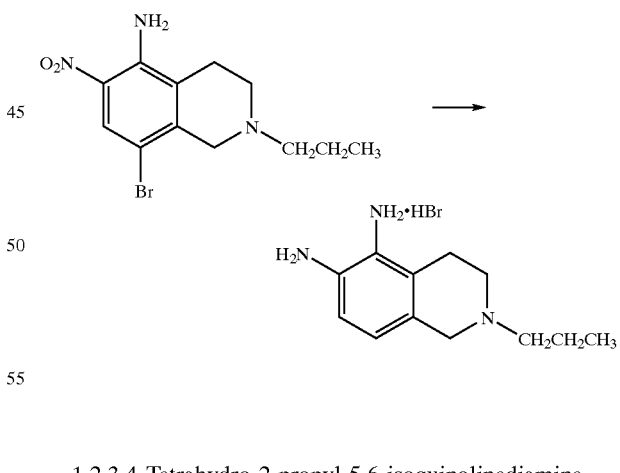

1,2,3,4-Tetrahydro-2-propyl-5,6-isoquinolinediamine

A solution of the product from Example 12 (1.50 g, 4.77 mmol) and 20% Pd on carbon (0.30 g) in 75 mL of MeOH was hydrogenated at room temperature and pressure for 24 hours. The reaction mixture was concentrated and the residue was suspended in iPr$_2$O and collected by filtration to give the title compound as a yellow solid (1.27 g, 93%).

EXAMPLE 19

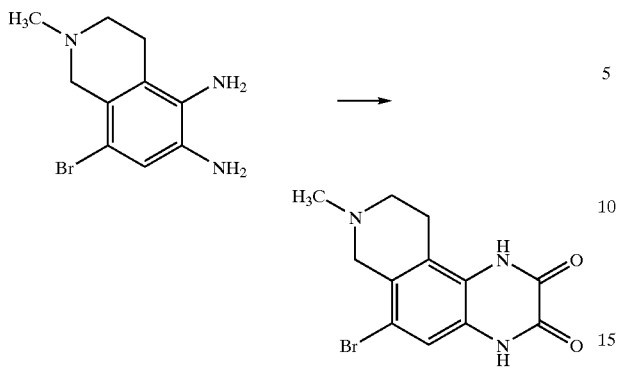

6-Bromo-1,4,7,8,9,10-hexahydro-8-methylpyrido[4,3-f]-quinoxaline-2,3-dione

A solution of the product from Example 13 (0.62 g, 2.56 mmol) and oxalic acid (0.23 g, 2.56 mmol) in 25 mL of 3N aqueous HCl solution were heated at reflux for 18 hours. The reaction mixture was cooled to room temperature and the solid which formed was collected by filtration and washed with cold water. The solid was recrystallized from hot water and dried under vacuum (100° C., $P_2O_5$) to give the title compound as a tan solid (0.191 g, 20%), mp=315–320° C. (dec.).

Analysis for ($C_{12}H_{12}BrN_3O_2 \cdot HCl \cdot H_2O$): Calc.: C, 39.53; H, 4.15; N, 11.53. Found: C, 39.19; H, 4.09; N, 11.21.

EXAMPLE 20

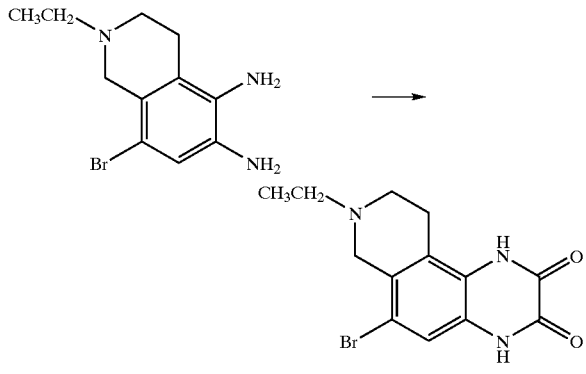

6-Bromo-8-ethyl-1,4,7,8,9,10-hexahydropyrido[4,3-f]-quinoxaline-2,3-dione

The product from Example 14 (0.88 g, 3.26 mmol) was converted to the title compound by the procedure described in Example 19. A white solid was obtained (0.71 g, 59%), np=325–350° C. (dec.).

Analysis for ($C_{13}H_{14}BrN_3O_3HCl \cdot 0.6H_2O$): Calc.: C, 42.03; H, 4.40; N, 11.31; Cl, 9.55. Found: C, 42.15; H, 4.39; N, 11.21; Cl, 9.57.

EXAMPLE 21

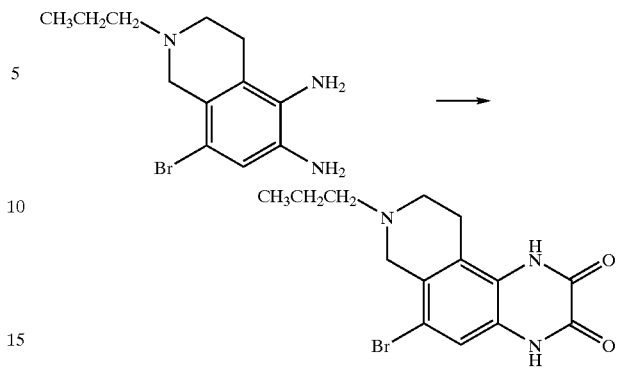

6-Bromo-1,4,7,8,9,10-hexahydro-8-propylpyrido[4,3-f]-quinoxaline-2,3-dione

The product from Example 15 (0.77 g, 2.71 mmol) was converted to the title compound by the procedure described in Example 19. A white solid was obtained.

Analysis for ($C_{14}H_{16}BrN_3O_2 \cdot 1.35HCl \cdot 0.4H_2O$) Calc.: C, 42.61; H, 4.64; N, 10.65; Br, 20.25; Cl, 12.13. Found: C, 42.74; H, 4.93; N, 10.42; Br, 19.68; Cl, 12.05.

EXAMPLE 22

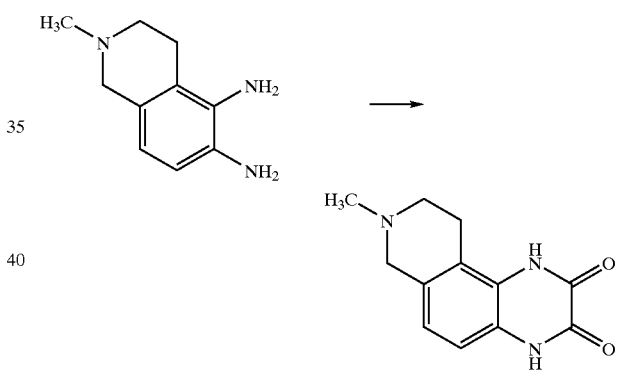

1,4,7,8,9,10-Hexahydro-8-methylpyrido[4,3-f]-quinoxaline-2,3-dione

The product from Example 16 (0.45 g, 2.54 mmol) was converted to the title compound by the procedure described in Example 19. A white solid was obtained (0.46 g, 68%), mp=310–335° C.

Analysis for ($C_{12}H_{13}BrN_3O_2 \cdot 0.95HCl \cdot 0.10H_2O$): Calc.: C, 53.84; H. 5.32; N, 15.70; Cl, 12.58. Found: C, 53.88; H, 5.30; N, 16.04; Cl, 12.46.

EXAMPLE 23

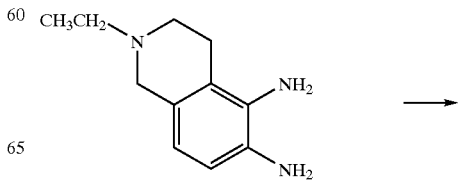

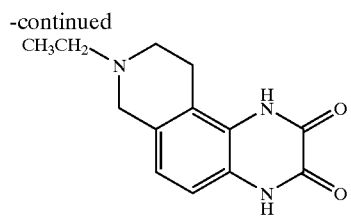

8-Ethyl-1,4,7,8,9,10-tetrahydropyrido[4,3-f]-quinoxaline-2,3-dione

The product from Example 17 (0.70 g, 3.66 mmol) was converted to the title compound by the procedure described in Example 19. A white solid was obtained (0.40 g, 38%), mp=325–330° C.

Analysis for ($C_{13}H_{15}BrN_3O_2 \cdot HCl \cdot 0.3H_2O$): Calc.: C, 54.38; H, 5.83; N, 14.63. Found: C, 54.50; H, 5.97; N, 14.72.

EXAMPLE 24

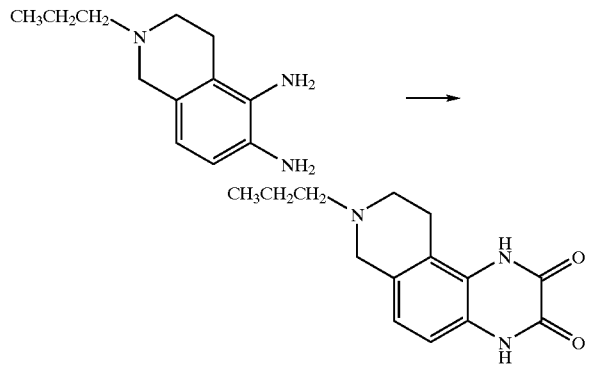

1,4,7,8,9,10-Hexahydro-8-propylpyrido[4,3-f]-quinoxaline-2,3-dione

The product from Example 18 (1.24 g, 4.33 mmol) was converted to the title compound by the procedure described in Example 19. A white solid was obtained (0.833 g, 65%), mp=340–350° C.

Analysis for ($C_{14}H_{17}N_3O_2 \cdot HCl \cdot 0.1H_2O$): Calc.: C, 56.51; H, 6.17; N, 14.12. Found: C, 56.62; H, 6.19; N, 14.19.

EXAMPLE 25

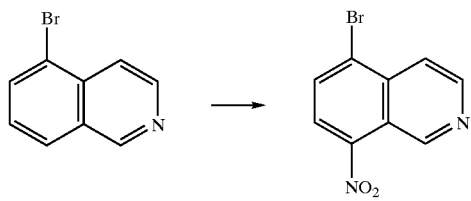

5-Bromo-8-nitroisoquinoline

The procedure described by Osborn AR, et al, *J Chem Soc* 1956:41191 was used. 5-Bromoisoquinoline (101 g, 0.485 mol) was dissolved in 300 mL concentrated $H_2SO_4$. $KNO_3$ (58.85 g, 0.582 mol) was dissolved in 200 mL of concentrated $H_2SO_4$ and added dropwise to the isoquinoline/acid solution. After addition, the reaction was stirred at room temperature for 2 hours. The reaction mixture was poured onto ice and the acid quenched carefully with the addition of $NH_4OH$ until the solution was strongly basic. The solids were dissolved in chloroform and filtered through a silica gel plug and eluted with chloroform. Evaporation, followed by trituration of the yellow solid with 5% ethyl acetate in hexane, gave the product (114.2 g, 93%).

$^1$H-NMR (200 MHz, $CDCl_3$) δ10.01 (s, 1H), 8.84 (d, 1H, J=5.9 Hz), 8.2 (d, 1H, J=8.1 Hz), 8.15 (d, 1H, J=5.6 Hz), 8.1 (d, 1H, J=8.2 Hz).

EXAMPLE 26

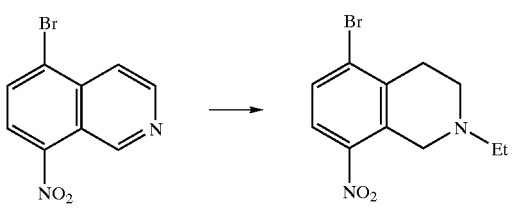

5-Bromo-2-ethyl-1,2,3,4-tetrahydro-8-nitroisoquinoline

A solution of 5-bromo-8-nitroisoquinoline (1 g, 3.95 mmol) in 20 mL THF was cooled to 0° C. and treated sequentially with sodium borohydride (0.75 g, 19.83 mmol) followed by the slow addition of acetic acid (20 mL). The reaction mixture was allowed to warm to room temperature, and an additional 2 equiv. of sodium borohydride was added. After quenching with water and treatment with sodium hydroxide solution to make basic, the reaction mixture was extracted with ethyl acetate. The organic residue was chromatographed on silica gel (25% ethyl acetate in hexane) to give the N-ethyl-5-bromo-8-nitrotetrahydroisoquinoline (0.8 g, 70% yield).

EXAMPLE 27

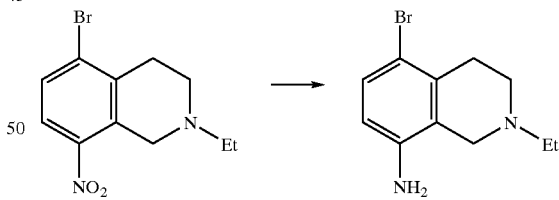

5-Bromo-2-ethyl-1,2,3,4-tetrahydro-8-isoquinolinamine

Raney nickel was refluxed in acetone for 2 hours prior to use to deactivate the metal. The product from Example 26 (0.1 g, 0.35 mmol) was dissolved in THF (10 mL), the Raney nickel added, and the reaction vessel charged with hydrogen gas. After stirring for 1 hour, the Raney nickel was removed by filtration and the solvent removed by filtration to give N-ethyl-5-bromo-8-aminotetrahydroisoquinoline (used without further purification).

EXAMPLE 28

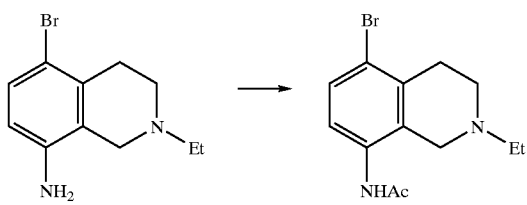

N-(5-bromo-2-ethyl-1,2,3,4-tetrahydro-8-isoquinolinyl)-acetamide

The product from Example 27 (0.35 mmol) was cooled in an ice bath, treated with acetic anhydride (10 mL), and stirred at room temperature under nitrogen overnight. Excess acetic anhydride was evaporated, the residue washed with ether, and evaporated. The white solid was triturated with ether and collected by filtration. The solid was washed with a mixture of ethyl acetate and saturated sodium bicarbonate. The organic layer was washed with sodium bicarbonate and sodium chloride solutions, dried over $MgSO_4$, filtered, and evaporated. The acetamide was obtained as a white solid (crystallized from ethyl acetate, 0.07 g, 67% yield).

EXAMPLE 29

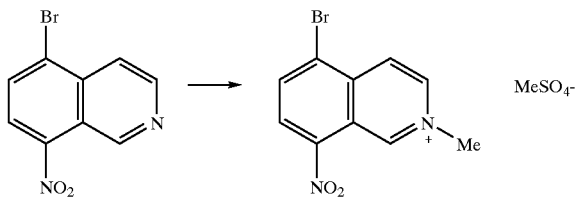

5-Bromo-2-methyl-8-nitro-2-isoquinolinium methanesulfonate

A mixture of 5-bromo-8-nitroisoquinoline (0.99 g, 3.91 mmol) and dimethylsulfate (0.41 mL) in anhydrous DMF (20 mL) was heated at 80° C. for 24 hours. After removing the DMF in vacuo, the isoquinoline methylammonium salt was obtained (used without further purification).

EXAMPLE 30

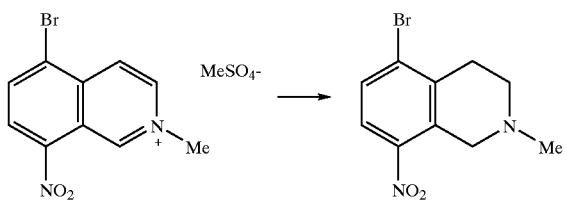

5-Bromo-1,2,3,4-tetrahydro-2-methyl-8-nitroisoquinoline

The product from Example 29 (3.9 mmol) was dissolved in acetic acid (10 mL) and sodium borohydride (0.15 g, 3.97 mmol) was added. After stirring for 24 hours, the reaction mixture was diluted with a mixture of ethyl acetate and water, and potassium carbonate was added portionwise to neutralize the acetic acid. The aqueous layer was extracted with ethyl acetate (2×), washed with saturated NaCl, dried over $MgSO_4$, filtered, and evaporated. The residue was chromatographed on silica gel (30% ethyl acetate in hexane) to give the light sensitive N-methyl-5-bromo-8-nitrotetrahydroisoquinoline (0.47 g, 45% yield).

EXAMPLE 31

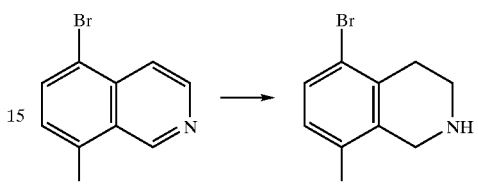

5-Bromo-1,2,3,4-tetrahydro-8-nitroisoquinoline

A mixture of 5-bromo-8-nitroisoquinoline (1.0 g, 3.95 mmol) and sodium borohydride (1.02 g, 26.96 mmol) in anhydrous THF (25 mL) at 0° C. was treated dropwise with formic acid (reaction turns from deep red to bright yellow). The reaction mixture was warmed to room temperature and stirred overnight in the dark. The reaction was quenched with water and basified with sodium hydroxide solution and then extracted with ethyl acetate (3×). The combined organic layers were washed with saturated NaCl, dried over $MgSO_4$, filtered, and evaporated. The residue was chromatographed on silica gel (65% ethyl acetate in hexane) to give the substituted tetrahydroisoquinoline (0.54 g, 53% yield).

Alternatively, a solution of 5-bromo-8-nitroisoquinoline (1.0 g) in glacial acetic acid (30 mL) was cooled to 0° C. and, before freezing, was treated with sodium cyanoborohydride (1.10 g). The reaction mixture was warmed slowly to room temperature under nitrogen. The reaction mixture was diluted with water and basified. Organic layer extracts were chromatographed on silica gel as before.

EXAMPLE 32

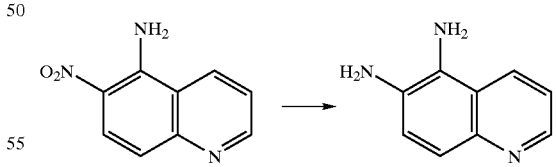

5,6-Quinolinediamine

A solution of 5-amino-6-nitroquinoline (25 g, 0.13 mol) in THF (500 mL) and methanol (500 mL) was treated with Raney nickel (7 g) under a hydrogen atmosphere (50.4 psi) on a Parr apparatus for 3.4 hours. Standard work-up gave the 5,6-diaminoquinoline.

EXAMPLE 33

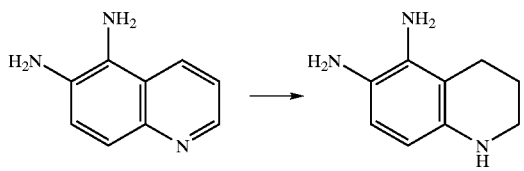

1,2,3,4-Tetrahydro-5,6-quinolinediamine

A solution of 5,6-quinolinediamine (12.5 g, 0.065 mol) and sulfuric acid (8 mL) in methanol (250 mL) was treated with platinum oxide (1 g) in a Parr apparatus under hydrogen for 16 hours. An additional 1 g portion of platinum oxide was added and hydrogenation continued for 44 hours additional. Standard work-up gave the 5,6-diaminotetrahydroquinoline.

EXAMPLE 34

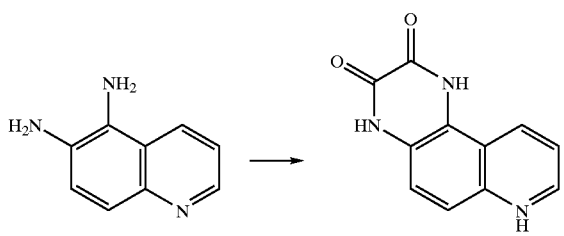

1,4-Dihydropyrido[3,2-f]quinoxaline-2,3-dione

A mixture of 5,6-quinolinediamine (11.3 g, 0.071 mol) and oxalic acid hydrate (17.9 g, 0.142 mol) in 200 mL 2N HCl was heated at reflux for 2 hours. The solid (12.3 g, 83% yield) was collected by filtration and washed consecutively with water and ether.

Analysis for ($C_{11}H_7N_3O_2.2H_2O$): Calc.: C, 53.07; H, 4.43; N, 16.88. Found: C, 52.99; H, 3.27; N, 16.88.

EXAMPLE 35

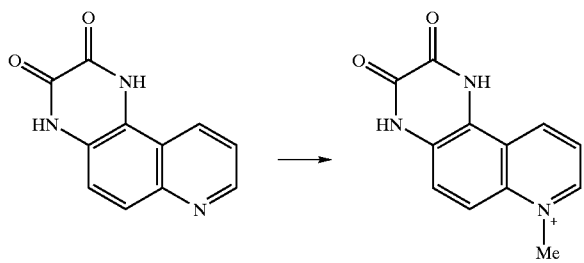

1,2,3,4-Tetrahydro-7-methyl-2,3-dioxopyrido[3,2-f]-quinoxalin-7-ium Methanesulfonate A mixture of the product from Example 34 (5 g, 23 mmol) and dimethylsulfate (3.7 g, 29 mmol) in DMF (40 mL) was heated at 100° C. for 20 hours. An additional portion of dimethylsulfate (3.5 g) was added, and the mixture was heated at 120° C. for 3 hours. After concentration, methanol was added and the solid collected by filtration to give the methylammonium derivative (6 g).

EXAMPLE 36

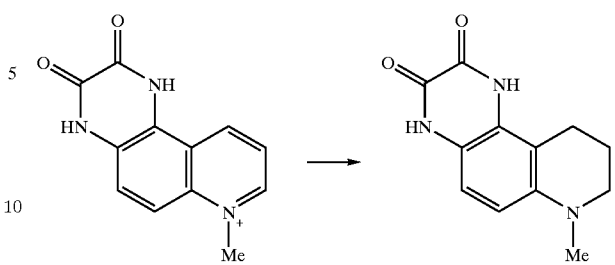

1,4,7,8,9,10-Hexahydro-7-methylpyrido[3,2-f]quinoxaline-2,3-dione

A mixture of the product from Example 35 (6 g, 18 mmol) and platinum oxide (0.5 g) in methanol (100 mL) was shaken on a Parr apparatus under a hydrogen atmosphere (52 psi) for 7.2 hours. After filtration, the solvent was evaporated to give a syrupy residue. The residue was triturated with water and the resulting solid collected by filtration and recrystallized from DMF/water to give the N-methyl derivative (1.7 g).

Analysis for ($C_{12}H_{13}N_3O_2.0.18H_2O$): Calc.: C, 61.44; H, 5.74; N. 17.91. Found: C, 61.44; H, 5.50; N, 17.75.

EXAMPLE 37

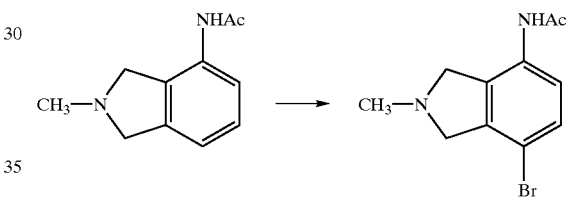

N-(7-bromo-2,3-dihydro-2-methyl-1H-isoindol-4-yl) acetamide

A solution of N-(2,3-dihydro-2-methyl-1H-isoindol-4-yl) acetamide (10 g) and bromine (3.0 g) in trifluoroacetic acid (150 mL) was stirred at 50° C. for 40 hours. The solution was evaporated in vacuo. The residue was dissolved in water (300 mL), and pH was adjusted to neutral with saturated $Na_2CO_3$. This treatment afforded a crystalline precipitate of the product, which was collected by filtration. Yield 9 g, mp 145–148° C.

In a similar manner was prepared:
N-[7-bromo-2-(1,1-dimethylethyl)-2,3-dihydro-1H-isoindol-4-yl]acetamide, mp 140–144° C.

EXAMPLE 38

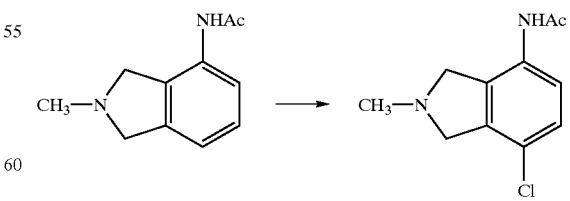

N-(7-chloro-2,3-dihydro-2-methyl-1H-isoindol-4-yl) acetamide

A mixture of N-(2,3-dihydro-2-methyl-1H-isoindol-4-yl) acetamide (20 g), hydrochloric acid (37%, 2.5 mL), and sodium chlorite (15%, 10 ml) in 96% ethanol (20 mL) was stirred at room temperature for 4 hours. The solvent was removed by evaporation, whereafter the residue was treated with saturated $Na_2CO_3$ in water to pH=7. The precipitated product was filtered off and washed with water and ether. Yield 1.1 g, mp 147–150° C.

EXAMPLE 39

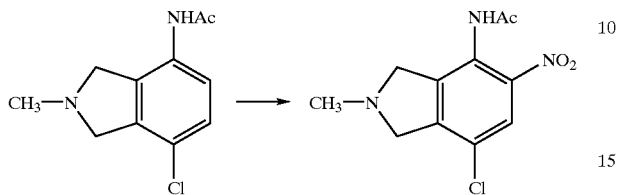

N-(7-chloro-2,3-dihydro-2-methyl-5-nitro-1H-isoindol-4-yl)acetamide

To a stirred 10° C. warm solution of $KNO_3$ (0.5 g) in sulphuric acid (10 mL) was added portionwise 4-acetamido-7-chloro-2-methyl-2H-1,2-dihydro-pyrrolo[3,4]benzene. In total 1 g. After additional stirring for 30 minutes at 10° C., the reaction mixture was poured on ice, and the resulting solution was neutralized with saturated $Na_2CO_3$. The precipitated product was then collected by filtration and washed with water. Yield 0.8 g, mp 165–166° C.

In a similar manner were prepared:
N-(7-bromo-2,3-dihydro-2-methyl-5-nitro-1H-isoindol-4-yl)acetamide, mp 161–163° C. and
N-(7-bromo-2,3-dihydro-2-(1,1-dimethylethyl)-5-nitro-1H-isoindol-4-yl)acetamide, mp 203–206° C.

EXAMPLE 40

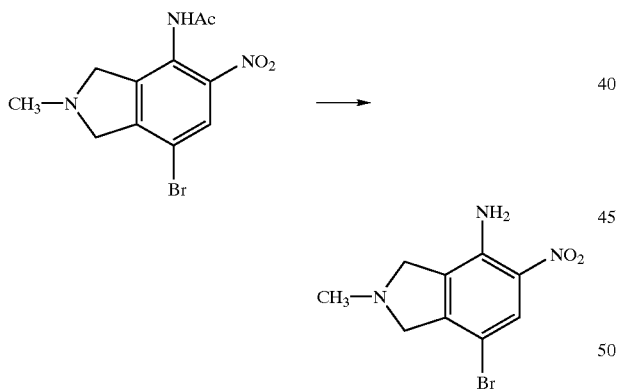

7-Chloro-2,3-dihydro-2-methyl-5-nitro-1H-isoindol-4-amine

A solution of N-(7-chloro-2,3-dihydro-2-methyl-1H-isoindol-4-yl)acetamide (1.5 g) in sulphuric acid (25 mL, 65%) was heated to 90° C. for 15 minutes, whereafter it was cooled to ambient temperature and neutralized with ammonia. This treatment left the product as a pale solid, which was isolated by filtration. Yield 1.1 g, mp 171–173° C.

In a similar manner were prepared:
7-Bromo-2,3-dihydro-2-methyl-5-nitro-1H-isoindol-4-amine, mp 174–176° C. and
7-Bromo-2,3-dihydro-2-(1,1-dimethylethyl)-5-nitro-1H-isoindol-4-amine, mp 220–221° C.

EXAMPLE 41

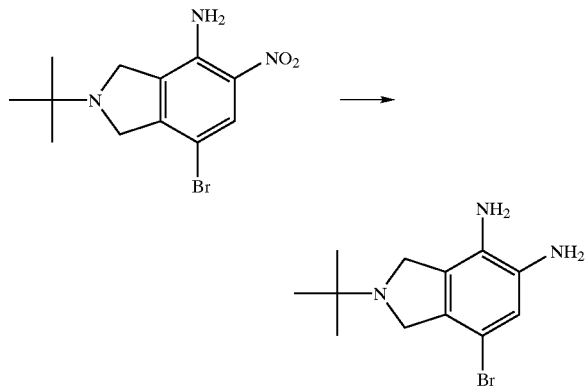

7-Bromo-2,3-dihydro-2-(1,1-dimethylethyl)-1H-isoindole-4,5-diamine

Hydrogenation of the nitro groups in the compounds of Example 40 were performed under standard conditions using RaNi as catalyst and ethanol as solvent. $H_2$ pressure 1 atm.

This afforded:
7-Bromo-2,3-dihydro-2-(1,1-dimethylethyl)-1H-isoindole-4,5-diamine hydrochloride, mp>300° C.;
7-chloro-2,3-dihydro-2-methyl-1H-isoindole-4,5-diamine, hydrochloride, mp 235–238° C.;
7-bromo-2,3-dihydro-2-methyl-1H-isoindole-4,5-diamine, hydrochloride, mp 90–95° C.; and
2,3-dihydro-2-methyl-1H-isoindole-4,5-diamine, hydrobromide, mp 198–200° C. Palladium on carbon (Pd/C) was used as catalyst.

EXAMPLE 42

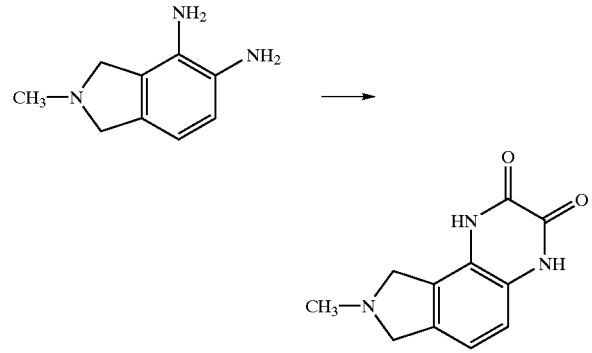

1,7,8,9-Tetrahydro-8-methyl-2H-pyrrolo[3,4-f]-quinoxaline-2,3 (4H)-dione

A solution of oxalic acid (1.3 g) and 4,5-diamino-1,3-dihydro-2-methyl-2H-pyrrolo[3,4]benzene, hydrobromide (1.5 g) in hydrochloric acid (4N, 20 mL) was refluxed for 4 hours. The reaction mixture was then reduced in vacuo to a volume of 10 mL, whereafter it was cooled on ice. The formed crystalline precipitate was collected by filtration and washed with water. Yield 1.25 g.

In a similar manner were prepared:
6-bromo-1,7,8,9-tetrahydro-8-methyl-2H-pyrrolo[3,4-f]quinoxaline-2,3(4H)-dione, mp>300° C.;

6-chloro-1,7,8,9-tetrahydro-8-methyl-2H-pyrrolo[3,4-f]quinoxaline-2,3(4H)-dione, mp>300° C.;

6-bromo-8-(1,1-dimethylethyl)-1,7,8,9-tetrahydro-2H-pyrrolo[3,4-f]quinoxaline-2,3(4H)-dione, mp>300° C.; and 2,3,4,7,8,9-hexahydro-8-methyl-2,3-dioxo-1H-pyrrolo[3,4-f]quinoxaline-6-sulfonamide, mp>300° C.

EXAMPLE 43

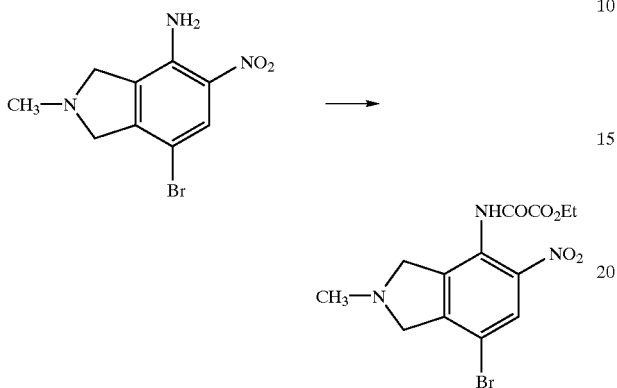

Ethyl [(7-bromo-2,3-dihydro-2-methyl-5-nitro-1H-isoindol-4-yl) amino]oxoacetate

To a stirred solution of triethylamine (0.83 mL) and 7-chloro-2,3-dihydro-2-methyl-5-nitro-1H-isoindol-4-amine (1.1 g) in THF (15 mL) was dropwise added a solution of ethyloxalylchloride (0.7 mL) in THF (5 mL). After the addition was completed, the reaction mixture was brought to reflux for 1 hour, then cooled to room temperature, whereafter the precipitate was removed by filtration. The filtrate was evaporated in vacuo. The residue was treated with 5 mL of ethanol which left the product as pale crystals. The crystals were collected by filtration. Yield 1.0 g, mp 153–154° C.

EXAMPLE 44

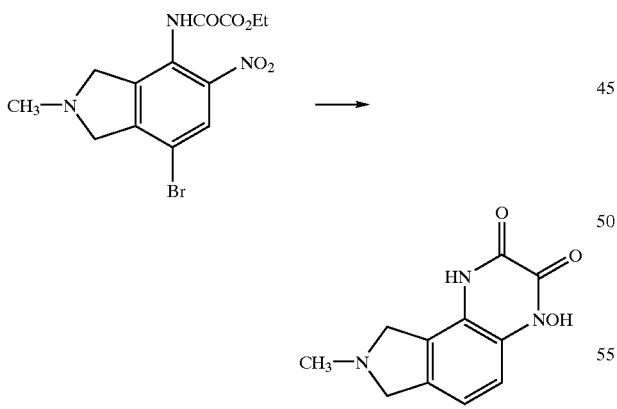

6-Bromo-1,7,8,9-tetrahydro-4-hydroxy-8-methyl-2H-pyrrolo[3,4-f]quinoxaline-2,3(4H)-dione The product of Example 43 was hydrogenated under standard conditions to give the above listed products.

The following compounds are prepared in a similar manner:

1,4,7,8,9,10-hexahydro-4-hydroxy-8-methylpyrido[4,3-]quinoxaline-2,3-dione and 1,4,7,8,9,10-hexahydro-4-hydroxy-9-methylpyrido[3,4-f]quinoxaline-2,3-dione.

EXAMPLE 44a

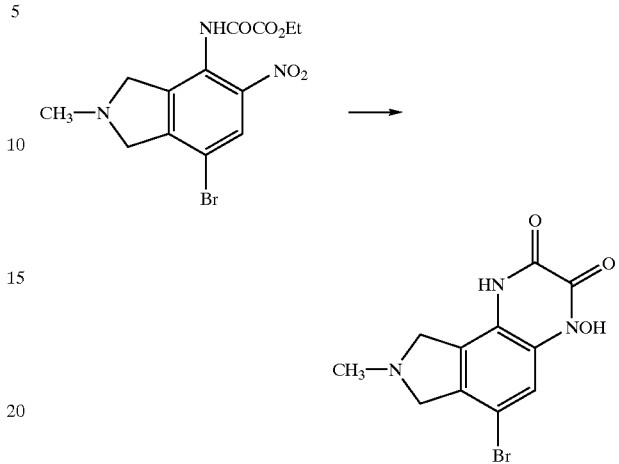

The following compounds are prepared in a similar manner:

6-Bromo-1,4,7,8,9,10-hexahydro-4-hydroxy-8-methylpyrido[4,3-f]quioxaline-2,3-dione and 6-Bromo-1,4,7,8,9,10-hexahydro-4-hydroxy-9-methylpyrido[3,4-f]quinoxaline-2,3-dione.

1,7,8,9-Tetrahydro-4-hydroxy-8-methyl-2H-pyrrolo[3,4-f]quinoxaline-2,3(4H)-dione The product of Example 43 was hydrogenated under standard conditions to give the above listed products.

EXAMPLE 45

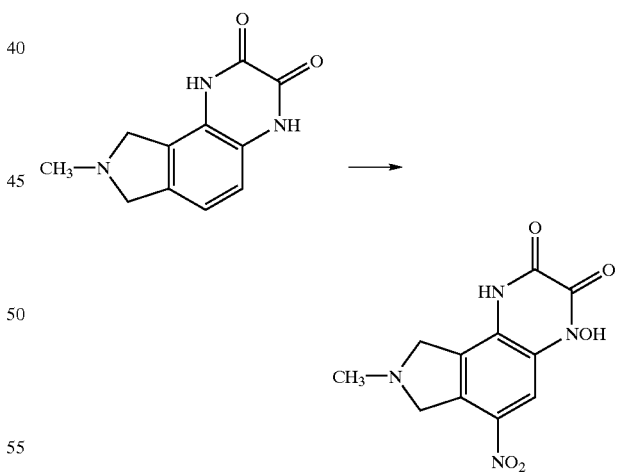

1,7,8,9-Tetrahydro-8-methyl-6-nitro-2H-iprrolo[3,4-f]-quinoxaline-2,3(4H)-dione

To a stirred 5° C. cold solution of potassium nitrate (0.2 g) in sulphuric acid (5 mL) was added 1,7,8,9-tetrahydro-8-methyl-2H-pyrrolo[3,4-f]-quinoxaline-2,3(4H)-dione (0.4 g). Stirring was continued for 15 minutes, whereafter the reaction mixture was poured on ice. The solution was now neutralized, whereby the product precipitated as a pale solid which was filtered off, mp>300° C.

EXAMPLE 46

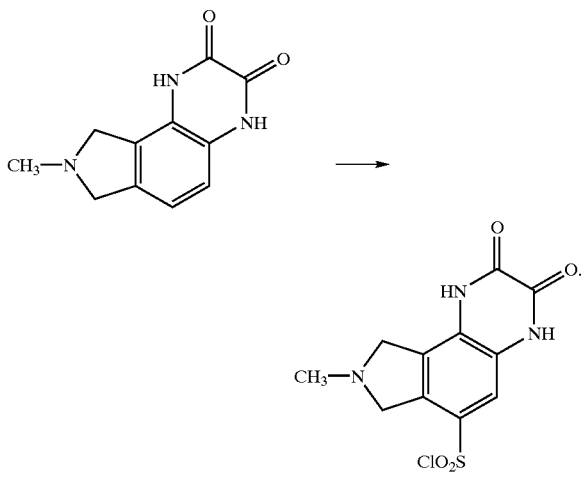

6-(Chlorosulfonyl)-1,7,8,9-tetrahydro-8-methyl-2H-pyrrolo[3,4-f]quinoxaline-2,3(4H)-dione A solution of 1,7,8,9-tetrahydro-8-methyl-2H-pyrrolo[3,4-f]quinoxaline-2,3(4H)-dione in chlorosulfonic acid was stirred at 120° C. for 3 hours, whereafter it was cooled and poured on ice. This afforded a crystalline precipitate of the product, which was filtered off and washed with water, mp>300° C.

EXAMPLE 47

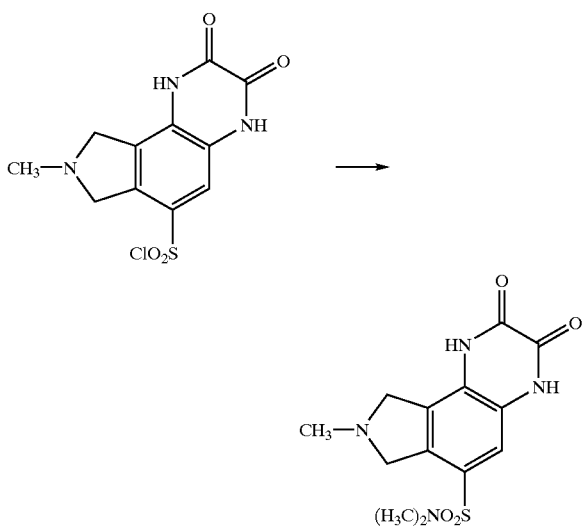

2,3,4,7,8,9-Hexahydro-N,N,8-trimethyl-2,3-dioxo-1H-pyrrolo[3,4-f]quinoxaline-6-sulfonamide The product of Example 46 (0.5 g) was slurred in tetrahydrofuran (10 mL) at room temperature while exposed to gaseous dimethylamine.

When the reaction had come to completion (monitored by TLC), the solvent was decanted from the oily precipitate. The precipitate was now treated with water which left the product as a white solid. The solid was filtered off and washed with water, mp 290–293° C.

In a similar manner were prepared the following sulfonamides:

4-[(2,3,4,7,8,9-hexahydro-8-methyl-2,3-dioxo-1H-pyrrolo[3,4-f]quinoxalin-6-yl)sulfonyl]morpholine, mp>300° C.;

1-[(2,3,4,7,8,9-hexahydro-8-methyl-2,3-dioxo-1H-pyrrolo[3,4-f]quinoxalin-6-yl)sulfonyl]pyrrolidine, mp>300° C.; and 2,3,4,7,8,9-hexahydro-8-methyl-2,3-dioxo-1H-pyrrolo[3,4-f]quinoxaline-6-sulfonamide, mp>300° C.

EXAMPLE 48

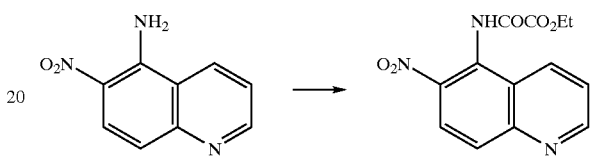

Ethyl [(6-nitro-5-quinolinyl)amino]oxoacetate

A solution of 5-amino-6-nitroquinoline (3 g, 16 mmol) in 50 mL DMF was treated with triethylamine (3.2 g, 32 mmol) and ethyl oxalylchloride (24 mmol) and then heated at 50° C. for 1 hour. A solid was removed by filtration, and the filtrate was concentrated in vacuo and treated with diethyl ether to precipitate a solid. A solid was collected by filtration and washed with ether (3.7 g, 80% yield).

EXAMPLE 49

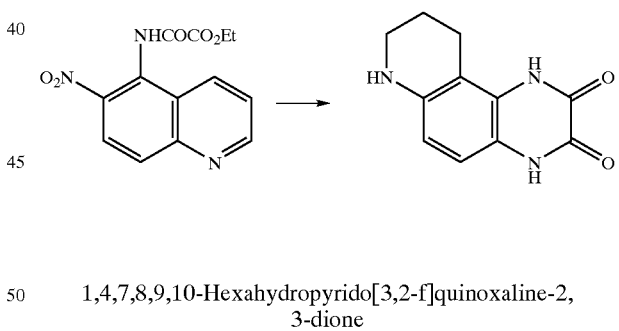

1,4,7,8,9,10-Hexahydropyrido[3,2-f]quinoxaline-2,3-dione

The reaction product, Example 48, was dissolved in 100 mL acetic acid, treated with $PtO_2$ (0.01 g), and then placed on a Parr apparatus under 51.1 psi hydrogen gas for 15.5 hours. Additional $PtO_2$ (0.15 g) was added and the apparatus recharged with hydrogen (52.7 psi). After a total of 47 hours, the catalyst was removed by filtration and washed with additional hot acetic acid. The filtrate was evaporated to a syrupy solid and then heated on a steam bath in methanol/ether. A solid (1 g, 38%) was collected by filtration and crystallized from methanol, DMF, and water and then washed with ether to give a light yellow solid, mp>285° C.

Analysis for $C_{11}H_{11}NO_2 \cdot 0.5H_2O$: Calc.: C, 58.40; H, 5.35; N, 18.57. Found: C, 58.70; H, 5.22; N, 18.63.

EXAMPLE 50

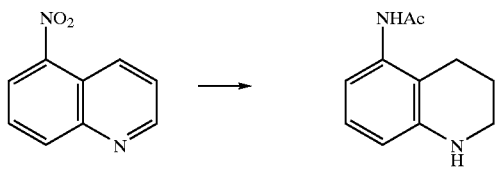

N-(1,2,3,4-tetrahydro-5-quinolinyl)acetamide

A solution of 5-nitroquinoline (50 g, 0.29 mol) in 1 L acetic acid and 30 mL acetic anhydride was treated with 5% Pd/C (3 g) and shaken on a Parr apparatus under a $H_2$ atmosphere (50.8 psi) for 10.4 hours. The reaction was then treated with $PtO_2$ (1 g) and recharged with $H_2$ (50.8 psi) and shaken an additional 2 hours. After removing the catalyst by filtration, the filtrate was evaporated and the residue was separated between methylene chloride and water. The aqueous layer was basified with 50% NaOH and washed with methylene chloride. The combined organic layer was dried over sodium sulfate, filtered, and evaporated. The resulting solid was crystallized from ethyl acetate (23 g, 42%).

EXAMPLE 51

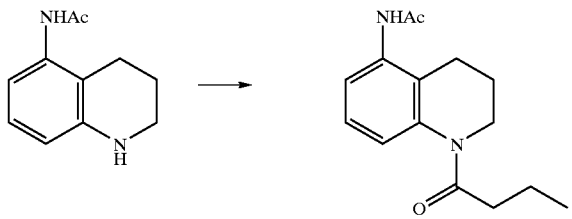

N-[1,2,3,4-tetrahydro-1-(1-oxobutyl)-5-quinolinyl]-acetamide

A mixture of the product from Example 50 (10 g, 53 mmol), butyric anhydride (12.5 g, 79 mmol), and triethylamine (10 g, 0.1 mol) in 50 mL methylene chloride was heated at reflux for 4 hours. The mixture was washed with water, and the organic layer was dried over sodium sulfate, filtered, and evaporated. The residue was chromatographed on silica gel (40–60% ethyl acetate in heptane as eluant) to give the product (9.5 g, 69%).

EXAMPLE 52

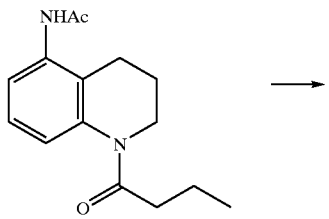

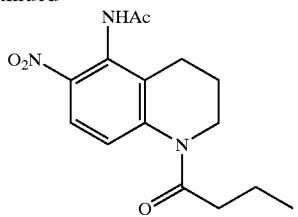

N-[1,2,3,4-tetrahydro-6-nitro-1-(1-oxobutyl)-5-quinolinyl]acetamide

A solution of the product from Example 51 (7.3 g, 28 mmol) in 50 mL acetic acid was treated with fuming nitric acid (10 mL) and stirred at room temperature for 1 hour. The reaction mixture was concentrated by rotoevaporation and added to a solution of potassium carbonate in water. After extraction with methylene chloride, the organic layer was dried over sodium sulfate, filtered, and evaporated. The residue was chromatographed on silica gel (40% ethyl acetate in heptane to 100% ethyl acetate as eluant). Obtained from the chromatography 4.5 g of the 6-nitro adduct, 2.2 g of mixture of the 6-nitro and 8-nitro products, and 1 g of the pure 8-nitro adduct.

EXAMPLE 53

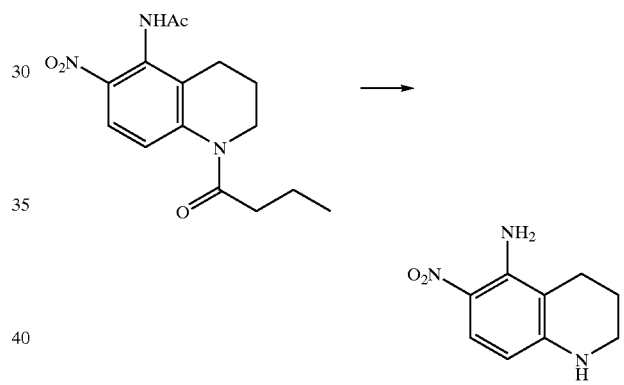

1,2,3,4-Tetrahydro-6-nitro-5-quinolinamine

The product from Example 52 (2.1 g, 6.9 mmol) was refluxed in 50 mL 2N HCl for 4 hours. The mixture was cooled and basified with 12.5% NaOH and then extracted with methylene chloride. Sodium chloride was added to the aqueous solution and then extracted again. The combined organic extracts were dried over sodium sulfate, filtered, and evaporated to an orange solid (1.29 g, 97%).

EXAMPLE 54

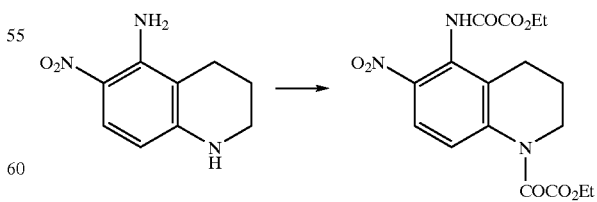

Ethyl [6-[(ethoxyoxoacetyl)amino]-3,4-dihydro-6-nitro-α-oxo-1(2H)-quinolineacetate A mixture of the product from Example 53 (1.29 g, 6.7 mmol), ethyl oxalylchloride (2.7 g, 20 mmol), and triethylamine (2.7 g, 2.7 mmol) in 40 mL THF was stirred at room temperature for 18 hours. The solvent was evaporated and the residue was extracted with methylene chloride/water. The organic layer was dried over sodium sulfate, filtered, and evaporated. The residue was chromatographed on silica gel (50% ethyl acetate in heptane as eluant) to give a syrup (2.8 g, 85%).

EXAMPLE 55

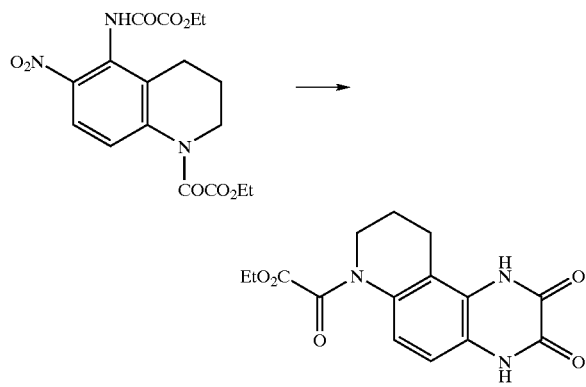

Ethyl 1,2,3,4,9,10-hexahydro-α,2,3-trioxopyrido[3,2-f]-quinoxaline-7(8H)-acetate A solution of the product from Example 54 (2.9 g) in 100 mL EtOH was treated with 5% Pd/C (1 g) and shaken on a Parr apparatus under a $H_2$ atmosphere (50.2 psi) for 40 minutes. After removing the catalyst by filtration, the filtrate was evaporated and the residue chromatographed on silica gel (10–50% ethyl acetate in heptane as eluant). Partially purified material from the column was triturated in hot toluene/MeOH. A solid (0.3 g, 14%) was collected by filtration, mp>285° C.

Analysis for $C_{15}H_{15}N_3O_5$: Calc.: C, 56.78; H, 4.77; N, 13.24. Found: C, 54.23; H, 4.82; N, 13.16.

EXAMPLE 56

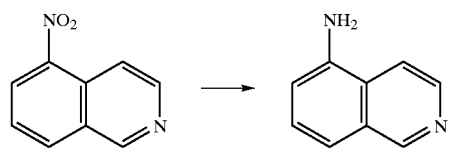

5-Isoquinolinamine

5-Nitroisoquinoline (100.3 g, 0.576 mol) was dissolved in MeOH and shaken with Raney nickel (10 g) on a Parr apparatus under a $H_2$ atmosphere (50 psi) for 21 hours. The MeOH was removed in vacuo, the residue dissolved in chloroform (150 mL), and filtered into 600 mL petroleum ether. The solid was collected by filtration. This trituration procedure was repeated several times to give 81.24 g (98%) of the desired product.

EXAMPLE 57

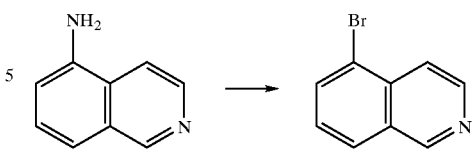

5-Bromoisoquinoline

The procedure described by Osborn AR, et al, *J Chem Soc* 1956:4191 was used. 5-Aminoisoquinoline (43.6 g, 0.302 mol) was dissolved in 300 ml 48% HBr and 200 mL water and cooled in an ice bath. $NaNO_2$ (21.21 g, 0.307 mol) in 130 mL of water was added dropwise to the HBr solution and the reaction stirred for 1 hour. CuBr (52 g, 0.363 mol) in 500 mL of 48% HBr was heated to 85° C., the diazonium solution added dropwise from an ice-cooled jacketed-addition funnel, and the reaction stirred overnight at 50° C. The reaction mixture was cooled in an ice bath and the acid neutralized by dropwise addition of concentrated $NH_4OH$ solution. The solid precipitates were filtered off, washed with concentrated $NH_4OH$ until colorless, and then water. The solid was dissolved in ethyl acetate, washed with brine (2×), and dried over magnesium sulfate, filtered, and evaporated. The reside was chromatographed on silica gel (30% ethyl acetate in hexane as eluant) to give 53.7 g (86%) of the product as an off-white solid.

EXAMPLE 58

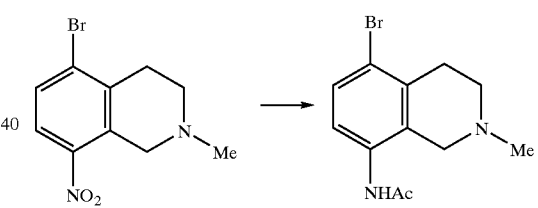

N-(5-bromo-1,2,3,4-tetrahydro-2-methyl-8-isoquinolinyl)acetamide

A solution of the product of Example 30 (6 g, 22.1 mmol) was dissolved in 100 mL THF. Raney nickel washed with acetone (2×5 mL) and THF (3×5 mL) was added and the reaction vessel purged with hydrogen. The reaction was stirred for 3 hours and freshly rinsed catalyst added. After 90 minutes, the reaction was complete. The catalyst was removed by filtration, washed with THF, and the filtrate evaporated. The residue was dissolved in 100 mL acetic anhydride and stirred for 72 hours. Excess acetic anhydride was removed in vacuo and the solid residue washed with ether. The solid was dissolved in chloroform and washed with saturated sodium bicarbonate. The organic layer was dried over magnesium sulfate, filtered, and evaporated. The solid was washed with ether and dried to give 5.03 g (80%) of the desired product, mp 192–194° C. (dec).

In a similar manner, N-5-bromo-2-ethyl-1,2,3,4-tetrahydro-8-isoquinolinyl)acetamide was prepared.

EXAMPLE 59

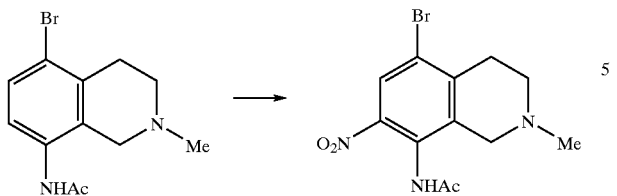

N-(5-bromo-1,2,3,4-tetrahydro-2-methyl-7-nitro-8-isoquinolinyl) acetamide

The product of Example 58 (4.93 g, 17.4 mmol) was dissolved in 85 mL trifluoroacetic acid, and then 20 mL fuming nitric acid was added over 2 hours. After stirring for 16 hours, the TFA/HONO$_2$ was removed in vacuo, and the residue was washed with chloroform and saturated sodium bicarbonate solution. The organic layer was dried over magnesium sulfate, filtered, and evaporated to give a light brown solid. This was washed with ether and dried to give 5.16 g (90%) of the desired product.

In a similar manner, N-(5-bromo-2-ethyl-1,2,3,4-tetrahydro-8-isoquinolinyl)acetamide was prepared.

EXAMPLE 60

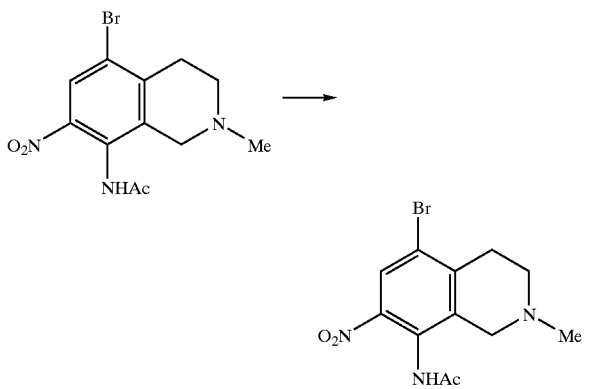

5-Bromo-1,2,3,4-tetrahydro-2-methyl-7-nitro-8-isoquinolinamine

The product from Example 59 (3.01 g, 9.17 mmol) was added to a cooled solution of sulfuric acid:water (50 mL:25 mL) and heated to 90° C. for 15 minutes. The reaction was cooled in an ice bath and poured onto ice. After the reaction mixture was neutralized with ammonium hydroxide, the solid was collected by filtration, washed with water and redissolved in ethyl acetate/THF, then dried over magnesium sulfate, filtered, and evaporated to give 2.48 g (95%) product.

Analysis for $C_{10}H_{12}BrN_3O_2 \cdot 0.35H_2O$: Calc.: C, 41.06; H, 4.37; N, 14.36. Found: C, 41.06; H, 4.16; N, 13.96.

In a similar manner, 5-bromo-2-ethyl-1,2,3,4-tetrahydro-7-nitro-8-isoquinolinamine was prepared.

EXAMPLE 61

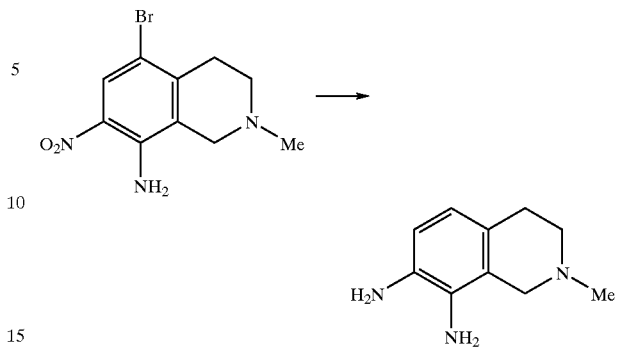

1,2,3,4-Tetrahydro-2-methyl-7,8-isoquinolinediamine

The product from Example 60 (1.0 g, 3.49 mmol) was suspended in 100 mL MeOH and treated with 20% Pd/C (0.2 g). The reaction mixture was purged with H$_2$ and stirred for 4 hours. The catalyst was removed by filtration and the filtrate was concentrated to give a brown solid (0.81 g, 90%).

In a similar manner, 2-ethyl-1,2,3,4-tetrahydro-7,8-isoquinolinediamine hydrobromide was prepared.

EXAMPLE 62

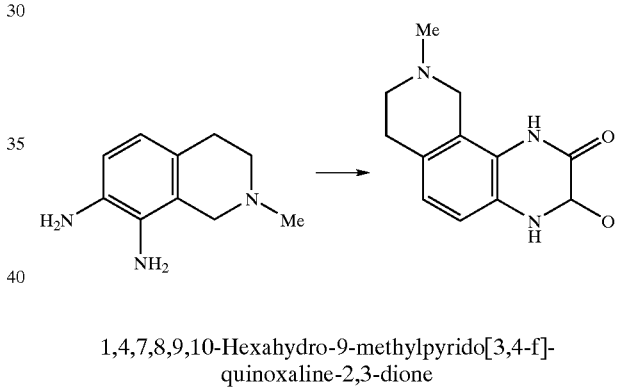

1,4,7,8,9,10-Hexahydro-9-methylpyrido[3,4-f]-quinoxaline-2,3-dione

The product from Example 61 (0.7 g, 2.71 mmol) and oxalic acid dihydrate (0.66 g, 5.24 mmol) in 25 mL 3N HCl were heated at reflux for 5 hours. After cooling to room temperature, the solids were collected by filtration, washed with cold water, and dried (0.5 g). Recrystallized from hot water, washed with ethyl acetate, and dried in vacuo over P$_2$O$_5$ to give 0.36 g (49%), mp>327° C., (>99.8% pure by C-18 reverse phase HPLC).

Analysis for $C_{12}H_{13}N_3O_2 \cdot HCl \cdot 0.4H_2O$: Calc.: C, 52.46; H, 5.42; N, 15.30; Cl, 12.89. Found: C, 42.47; H, 5.20; N, 15.16; Cl, 11.09.

In a similar manner, the 9-ethyl-1,4,7,8,9,10-hexahydropyrido[3,4-f]quinoxaline-2,3-dione was prepared.

Analysis for $C_{13}H_{15}N_3O_2 \cdot HCl$: Calc.: C, 55.42; H, 5.72; N, 14.91; Cl, 12.58. Found: C, 54.73; H, 5.81; N, 14.84; Cl, 11.95. (>99.9% pure by C-18 reverse phase HPLC).

In a similar manner, 6-bromo-9-ethyl-1,4,7,8,9,10-hexahydropyrido[3,4-f]quinoxaline-2,3-dione was prepared.

Analysis for $C_{12}H_{12}BrN_3O_2 \cdot HCl$: Calc.: C, 41.58; H, 3.78; N, 12.12. Found: C, 41.20; H, 3.80; N, 11.97.

In a similar manner, 6-bromo-1,4,7,8,9,10-hexahydro-9-methylpyrido[3,4-f]-quinoxaline-2,3-dione was prepared.

Analysis for $C_{13}H_{14}BrN_3O_2 \cdot CH_3SO_3H$: Calc.: C, 40.01; H. 4.32; N, 10.00; S, 7.63. Found: C, 39.70; H, 4.26; N, 9.89; S, 7.13.

EXAMPLE 63

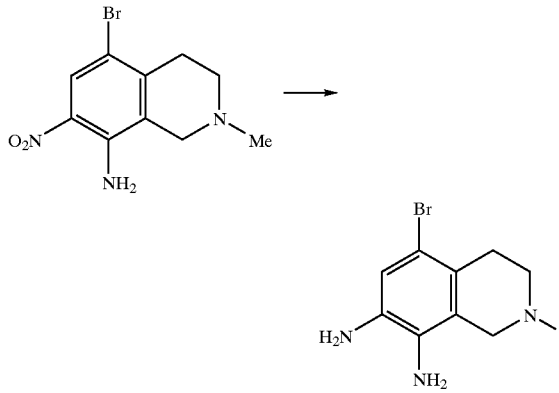

5-Bromo-1,2,3,4-tetrahydro-2-methyl-7,8-isoquinolinediamine

A solution of the product from Example 60 (1.02 g, 3.49 mmol) in 50 mL THF was treated with Raney nickel (prewashed with acetone followed by THF), and the reaction vessel was purged with $H_2$. After stirring for 2.5 hours, the catalyst was removed by filtration and the filtrate evaporated to give a tan oil. The product was used without further purification.

In a similar manner, 5-bromo-2-ethyl-1,2,3,4-tetrahydro-8-isoquinolinediamine was prepared.

EXAMPLE 64

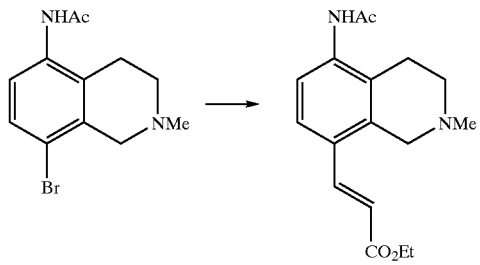

Ethyl 3-[5-acetylamino)-1,2,3,4-tetrahydro-2-methyl-8-isoquinolinyl]-2-propenoate A solution of the product from Example 5 (2.00 g, 7.06 mmol) in 25 mL of acetonitrile and 5 mL of triethylamine was treated with ethylacrylate (2.0 mL) and bis(triphenylphosphine)palladium(II) chloride (0.30 g). The resulting solution was heated at reflux for 72 hours. The reaction mixture was cooled and dissolved in chloroform. The organic phase was washed with saturated aqueous sodium bicarbonate, dried ($Na_2SO_4$), and concentrated. The residue was crystallized from acetonitrile to give 0.94 g (44%) of the desired product.

EXAMPLE 65

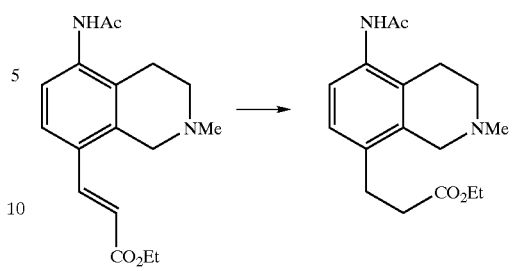

Ethyl 5-(acetylamino)-1,2,3,4-tetrahydro-2-methyl-8-isoquinolinepropanoate

A solution of the product from Example 64 (0.90 g, 2.98 mmol) was dissolved in tetrahydrofuran and hydrogenated at 52 psi over 5% Pd/C for 16.4 hours. The reaction mixture was filtered and concentrated to give 0.65 g (72%) of the desired product.

EXAMPLE 66

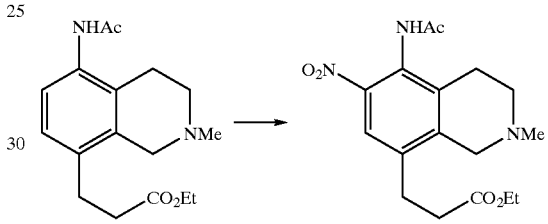

Ethyl 5-(acetylamino-1,2,3,4-tetrahydro-2-methyl-7-nitro-8-isoquinolinepropanoate A solution of the product from Example 65 (0.50 g, 1.65 mmol) in 5 mL of trifluoroacetic acid was treated with 0.5 mL of fuming nitric acid dropwise. The resulting solution was stirred at room temperature for 18 hours. The reaction mixture was concentrated and the residue dissolved using chloroform/saturated aqueous $NaHCO_3$ solution. The organic phase was separated, and the aqueous phase was extracted with additional chloroform. The combined organic extracts were dried ($Na_2SO_4$) and concentrated. The residue was purified by chromatography ($SiO_2$, 20.1:1 $CHCl_3$:EtOH:$Et_3N$) to give 0.52 g (90%) of the desired product.

EXAMPLE 67

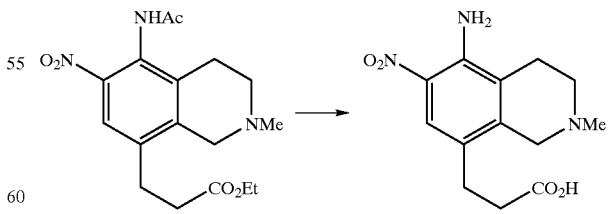

5-Amino-1,2,3,4-tetrahydro-2-methyl-7-nitro-8-isoquinolineproyanoic acid

The product from Example 66 is converted to the desired product by the method described in Example 66.

EXAMPLE 68

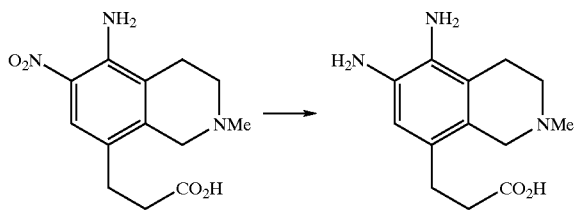

5,6-Diamino-1,2,3,4-tetrahydro-2-methyl-8-isoquinolinepropanoic acid

The product from Example 67 is converted to the desired compound by the method described in Example 67.

EXAMPLE 69

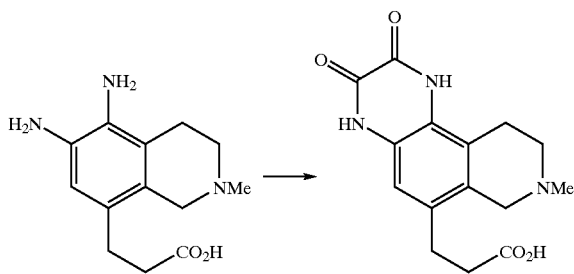

1,2,3,4,7,8,9,10-octahydro-8-methyl-2,3-dioxopyrido[4,3-f]quinoxaline-6-propanoic acid The product from Example 68 is converted to the desired compound by the method described in Example 62.

EXAMPLE 70

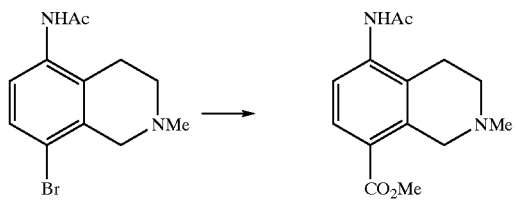

Methyl [8-(2-methyl-5-acetamido-1,2,3,4-tetrahydroisoquinolinyl)]carboxylic acid A solution of the product from Example 5 (0.76 g, 2.70 mmol) in 50 mL of acetonitrile, 0.75 mL MeOH, and 1.3 mL of triethylamine was treated with bis(triphenylphosphine)palladium(II) chloride (0.30 g). The resulting solution was placed in a high pressure reactor, charged to 800 psi with carbon monoxide, and heated at 120° C. for 8 days. The reaction mixture was cooled and dissolved in chloroform. The organic phase was washed with saturated aqueous sodium bicarbonate, dried ($Na_2SO_4$), and concentrated. The residue was purified by chromatography ($SiO_2$, 10:1:1 $CHCl_3$:EtOH:$Et_3$N) to give 0.26 g (37%) of the desired product.

EXAMPLE 71

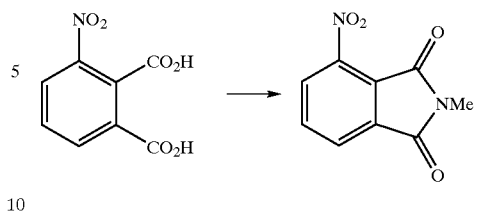

Ethyl S-(acetylamino)-1,2,3,4-tetrahydro-2-methyl-7-nitro-8-isoquinolinepropanoate A 3 L 3-neck flask was charged with 3-nitro-phthalic acid (502 g, 2.38 mol) and 1,3-dimethyl urea (230 g, 2.62 mol). This was heated slowly to 170° C. then allowed to cool. One liter ethanol was added to the reaction product before it solidified. The product which crystallized was filtered, washed with ethanol and ether, and air dried to a yellow powder, 420.7 g. A second crop was 50.4 g for a yield of 96%.

EXAMPLE 72

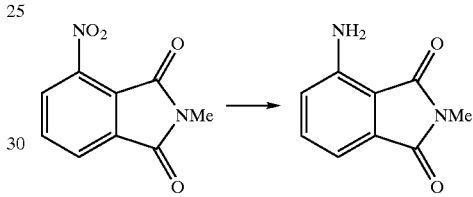

4-Amino-2-methyl-1H-isoindole-1,3(2H)-dione

A pressure reactor was charged with 2-methyl-4-nitro-1H-isoindole-1,3(2H)-dione (59.0 g, 0.286 mol), 1 L acetic acid, and 2 q 5% Pd/C. The reactor was pressurized to 48 psi hydrogen, and the exothermic reaction was complete in 2 hours. The catalyst was removed with hot filtration, and the filtrate combined with the contents of another reactor which contained 53.2 g of 3-nitrophthalimide under the same conditions. The acetic acid was removed at the rotovap, then the salt was cracked by adding 2 M ammonium hydroxide. The slurry was stirred 30 minutes; then filtered; washed with water, ethanol, and ether; and dried at the pump to give 91.4 g, 95% of the product.

EXAMPLE 73

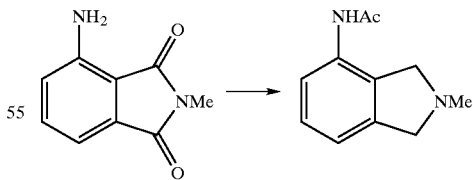

2,3-Dihydro-2-methyl-1H-isoindol-4-amine

A 5-L flask was set up with an overhead stirrer, temperature probe, and 500-mL addition funnel. The flask was charged with lithium aluminum hydride (100 g) and anhydrous tetrahydrofuran (1.5 L). The resulting suspension was treated with 4-amino-2-methyl-1H-isoindole-1,3(2H)-dione (100 g, 0.56 mol) at a rate such that the reaction did not become too vigorous. The resulting suspension was heated at reflux for 18 hours. The reaction vessel was cooled, placed in an ice bath, and cautiously quenched with 100 mL water, 100 mL 1N NaOH, and 300 mL water. The resulting suspension was treated with chloroform (1.5 L) and the pH of the suspension adjusted to 12 with 50% aqueous sodium hydroxide solution. The resulting suspension was treated with acetic anhydride (300 mL) while maintaining the pH at approximately 12. The reaction mixture was treated with sodium sulfate (800 g) and potassium carbonate (200 g), and the reaction mixture was filtered. The filter cake was washed with additional chloroform, and the combined filtrates were concentrated. The residue was crystallized from ethyl acetate to give 71 g (66%) of the desired product, mp 157° C.

EXAMPLE 74

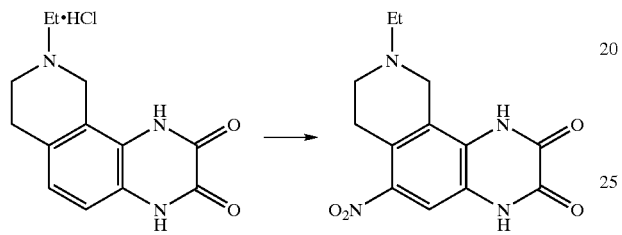

9-Ethyl-1,4,7,8,9,10-hexahydro-6-nitro-pyrido[3,4-f]quinoxaline-2,3-dione

A solution of 9-ethyl-1,4,7,8,9,10-hexahydro-pyrido[3,4-f]quinoxaline-2,3-dione (0.61 g, 2.16 mmol) in 20 mL of concentrated sulfuric acid was treated with a solution of potassium nitrate (0.25 g, 2.47 mmol) in 2 mL concentrated sulfuric acid. After stirring for 3 hours at room temperature, the reaction mixture was poured onto ice and cooled in an isopropyl alcohol/dry ice bath. Ammonium hydroxide was added to adjust the pH to 8.9, and the yellow solid was collected by filtration (0.59 g, 94% yield).

EXAMPLE 75

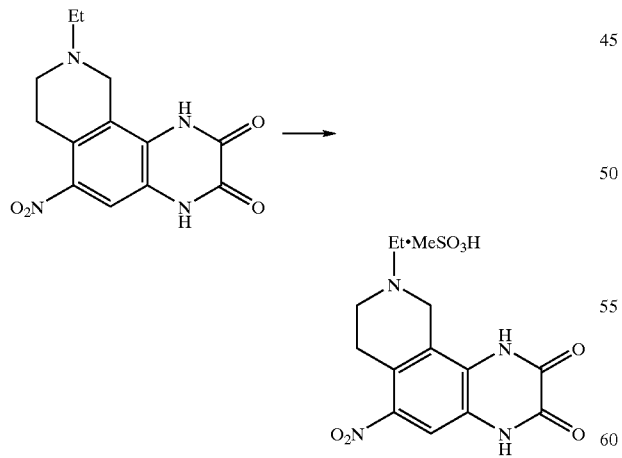

9-Ethyl-1,4,7,8,9,10-hexahydro-6-nitro-pyrido-[3,4-f]quinoxaline-2,3-dione methanesulfonate The product from Example 74 was suspended in 300 mL dimethylformamide and 1 mL of 3 N methanesulfonic acid added. The suspension was warmed to 100° C. The colour changed from orange to yellow and all of the solid dissolved. Solvent was evaporated in vacuo, the yellow residue washed with acetone and then dried under vacuum over $P_2O_5$ to give the title compound (0.73 g, 92% yield) mp=302–304° C.

Analysis for $C_{13}H_{14}N_4O_4 \cdot 1.07\ CH_3SO_3H \cdot 0.25H_2O$: Calc: C, 42.54; H, 4.76; N, 14.11; S, 8.60. Found: C, 42.54; H, 4.72; N, 14.27; S, 8.60.

EXAMPLE 76

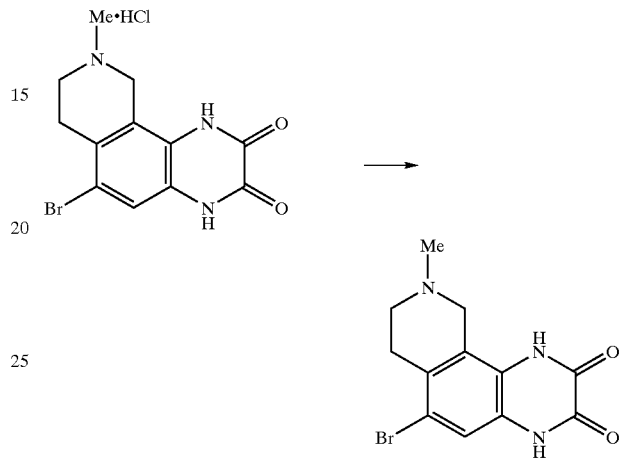

6-Bromo-1,4,7,8,9,10-hexahydro-9-methyl-pyrido-[3,4-f]quinoxaline-2,3-dione methansulfonate 6-Bromo-1,4,7,8,9,10-hexahydro-9-methylpyrido-[3,4-f]-quinoxaline-2,3-dione hydrochloride (3.16 g, 9.12 mmol) was dissolved in 1.8 L boiling water and treated with sodium bicarbonate (0.8 g, 9.2 mmol). The mixture was cooled and placed in a 5° C. freezer. The precipitate was collected, washed with acetone and ether and dried to give the title compound (2.17 g, 77% yield).

EXAMPLE 77

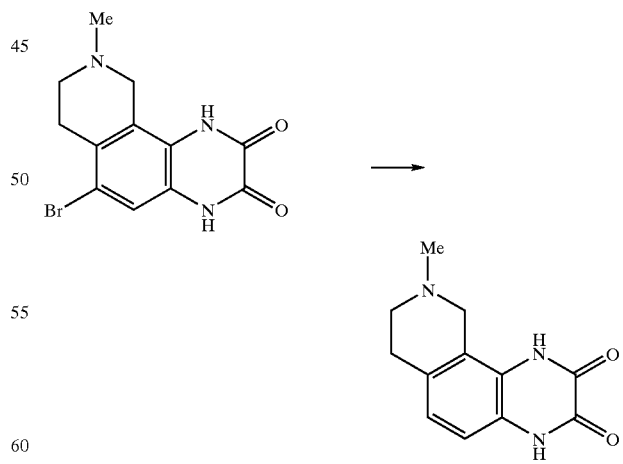

1,4,7,8,9,10-Hexahydro-9-methyl-pyrido-[3,4-f]quinoxaline-2,3-dione monohydrochloride The product from Example 76 (1.25 g) and 20% Pd/C (0.5 g) in 100 mL dimethylformamide was shaken on a Parr apparatus under 52 psi H$_2$ (g) for 15.5 hours. After filtration of the catalyst, the solvent was removed and the residue washed with ether and ether/acetone. The tan solid was dissolved in a minimum of water and neutralized with 5 drops of ammonium hydroxide which induce slow precipitation. The solid was again collected and washed with water/acetone to give of the title compound (0.65 g, 70% yield).

EXAMPLE 78

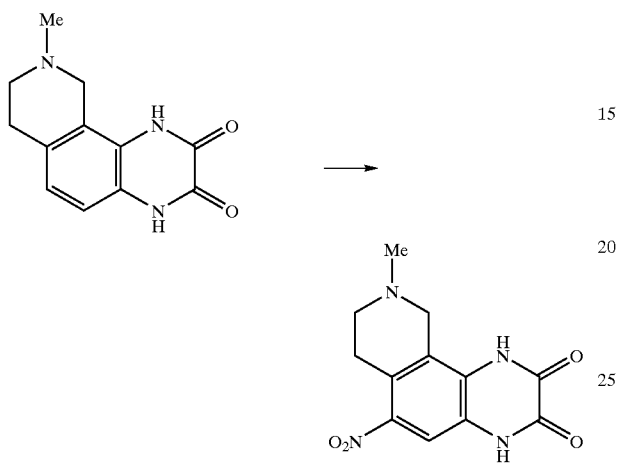

1,4,7,8,9,10-Hexahydro-9-methyl-6-nitro-pyrido-[3,4-f]quinoxaline-2,3-dione methansulfonate A solution of the product from Example 77 (0.64 g, 2.77 mmol) in 20 mL concentrated sulfuric acid was treated with potassium nitrate (0.29 g, 2.87 mmol) in 2 mL concentrated sulfuric acid. After stirring overnight at room temperature the reaction mixture was poured onto ice, cooled in a dry ice bath, and then basified with ammonium hydroxide to pH 8.9. The orange/yellow solid was collected by filtration and washed consecutively with water, acetone and ether and dried to give the title compound (0.78 g, 100% yield).

EXAMPLE 79

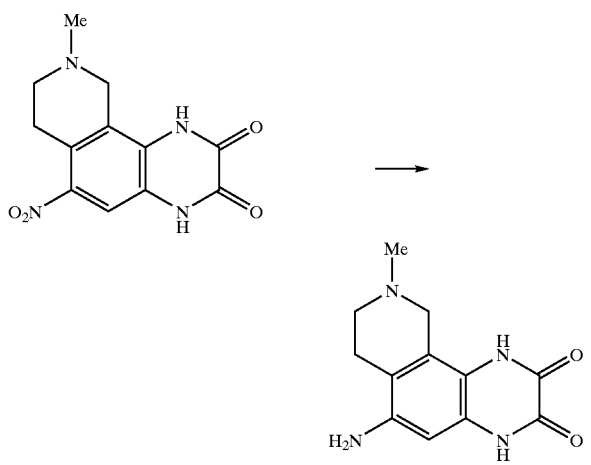

6-Amino-1,4,7,8,9,10-hexahydro-9-methyl-pyrido-[3,4-f]quinoxaline-2,3-dione

A solution of the product from Example 78 (0.77 g, 2.79 mmol) in 100 mL acetic acid was treated with 5% Pd/C (0.1 g) and shaken on a Parr apparatus at 52 psi for 9.5 hours. After removing the catalyst by filtration, the solvent was removed and the residue recrystallized from water to give the mono acetic acid salt (0.14 g). The filtrate was basified to pH 9 with ammonium hydroxide to precipitate the free base, which was further washed with water and then ether to give the title compound as a brown solid (0.46 g).

EXAMPLE 80

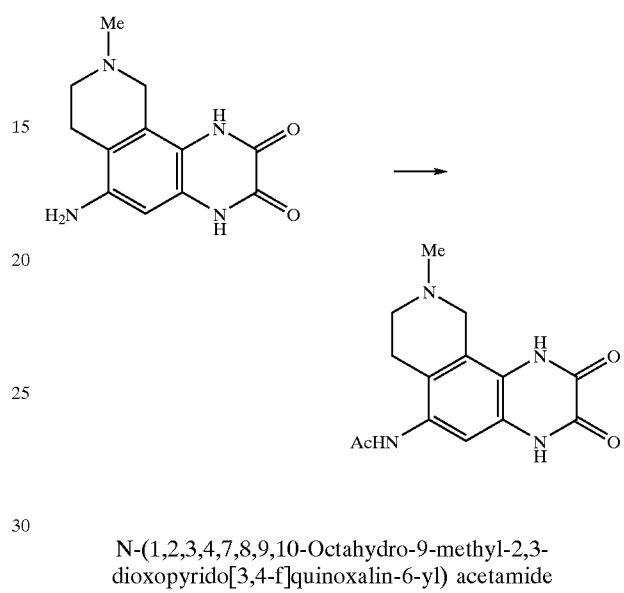

N-(1,2,3,4,7,8,9,10-Octahydro-9-methyl-2,3-dioxopyrido[3,4-f]quinoxalin-6-yl) acetamide A mixture of the product from Example 79 (0.27 g, 1.1 mmol) in 25 mL acetic acid and 10 mL acetic anhydride was stirred at room temperature for 18 hours. After removing the solvent, the residue was washed with ether, dissolved in water and then basified with saturated sodium bicarbonate. The flask was cooled in the freezer for 2 hours and the precipitate collected by filtration, washed consecutively with water and ether, and dried over P$_2$O$_5$ in vacuo to give the title compound (0.2 g).

EXAMPLE 81

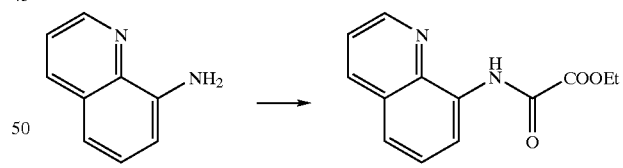

Oxo[(8-quinolinyl)amino]acetic acid ethyl ester

A mixture of 8-aminoquinoline (14.4 g, 0.1 mol), ethyloxalyl chloride (16.4 g, 0.12 mol) and triethylamine (15 g, 0.15 mol) in 150 mL chloroform was stirred at room temperature for 18 hours. The mixture was washed with water and extracted with methylene chloride. The combined organic layers were washed with saturated NaCl solution, dried over sodium sulfate, filtered and evaporated. The residue was then crystallized from toluene/heptane to give the title compound (20.6 g, 861 yield).

Analysis for C$_{13}$H$_{12}$N$_2$O$_3$: Calc: C, 63.93; H. 4.95; N, 11.47. Found: C, 63.20; H. 5.12; N, 11.35.

EXAMPLE 82

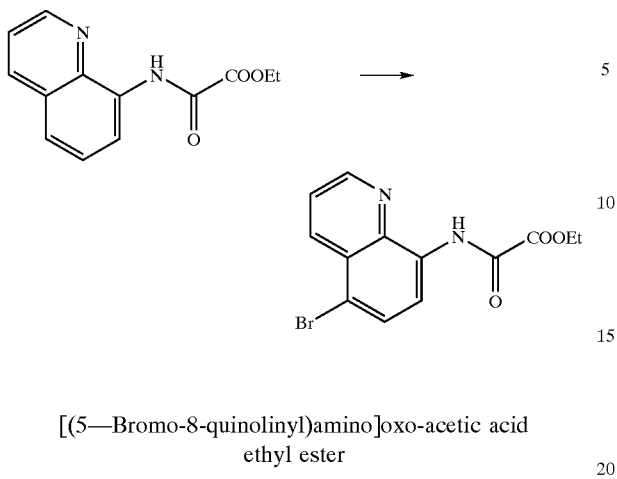

[(5—Bromo-8-quinolinyl)amino]oxo-acetic acid ethyl ester

A solution of the product from Example 81 (20 g, 82 mmol) in 200 mL acetic acid was treated with a solution of bromine (15.7 g, 0.198 mol) in 50 mL of acetic acid and stirred at room temperature for 1 hour. The solid was collected by filtration and washed with ether to give the title compound (23.5 g, 69% yield).

EXAMPLE 83

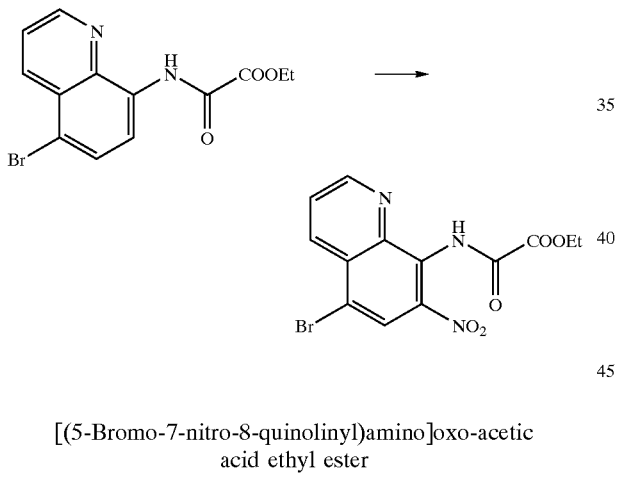

[(5-Bromo-7-nitro-8-quinolinyl)amino]oxo-acetic acid ethyl ester

A solution of the product from Example 82 (23.5 g, 58 mmol) in 30 mL fuming nitric acid and 150 mL trifluoroacetic acid was heated at 80° C. for 18 hours. The solvent was removed and the residue was treated with water to give a solid. The solid was collected by filtration and washed with ether and dried to give the title compound (9.5 g, 45% yield).

EXAMPLE 84

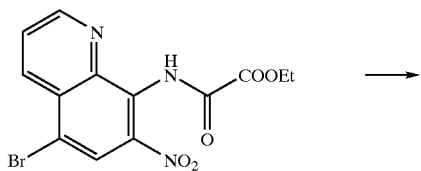

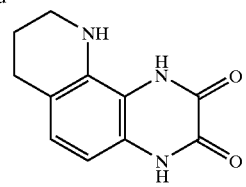

1,4,7,8,9,10-Hexahydro-pyrido[2,3-f]quinoxaline-2,3-dione

A solution of the product from Example 83 (1 g, 2.7 mmol) in 250 mL acetic acid was treated with 20% Pd/C (0.1 g) and shaken on a Parr apparatus under 52 psi hydrogen gas for 21 hours. After removal of the catalyst, the solvent was evaporated but gave negligible material. The catalyst/celite was washed two times with 1 N HCl, and the aqueous solution was basified with sodium bicarbonate. The precipitate was collected by filtration, dried and then recrystallized from methanol/dimethylformamide to give the title compound (0.26 g, 44% yield) mp>300° C.

Analysis for $C_{11}H_{11}N_3O_2 \cdot 1.5H_2O$: Calc: C, 54.09; H, 5.78; N, 17.20. Found: C, 54.20; H, 5.82; N, 17.17.

EXAMPLE 85

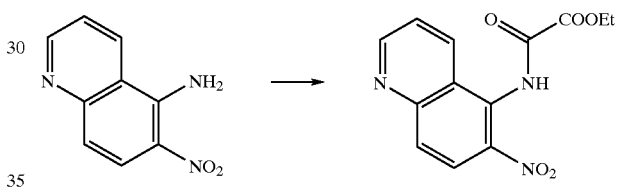

[(6-Nitro-5-quinolinyl)amino]oxo-acetic acid ethyl ester

A solution of 5-amino-6-nitroquinoline (3 g, 16 mmol) in 50 mL dimethylformamide was treated with triethylamine (3.2 g, 32 mmol) and ethyloxalyl chloride (3.2 g, 24 mmol) and heated at 50° C. for 1 hour. After removing the triethylamine hydrochloride by filtration, the filtrate was concentrated and diethyl ether added. The title compound (3.7 g, 80% yield) was collected by filtration.

EXAMPLE 86

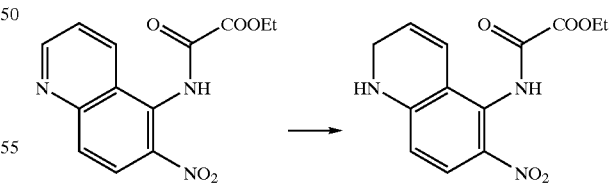

[(1,2-Dihydro-6-nitro-5-quinolinyl)amino]oxo-acetic acid ethyl ester

A solution of the product from Example 85 (5 g, 17.5 mmol) in 80 mL acetic acid was treated with sodium cyanoborohydride (2.2 g, 35 mmol) portionwise under an argon atmosphere and stirred for 4 hours. Water (100 mL) was added to the reaction mixture, and the resulting solid was collected by filtration and dried (3.9 g, 78% yield).

EXAMPLE 87

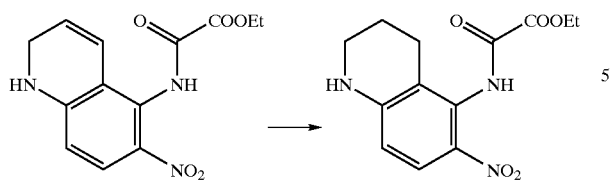

[(1,2,3,4-Tetrahydro-6-nitro-5-quinolinyl)amino]
oxo-acetic acid ethyl ester

A solution of the product form Example 86 (4.8 g, 16.5 mmol) in 250 mL tetrahydrofuran was treated with triphenylphosphine (5 g) and rhodium trichloride (0.83 g) and shaken in a Parr apparatus under a hydrogen atmosphere (54 psi) for 40 minutes. The solvent was evaporated and the residue was purified by silica gel chromatography (4:1 to 1:1 heptane:ethyl acetate as eluant) to give the title compound as a red solid (4.22 g, 87% yield).

EXAMPLE 88

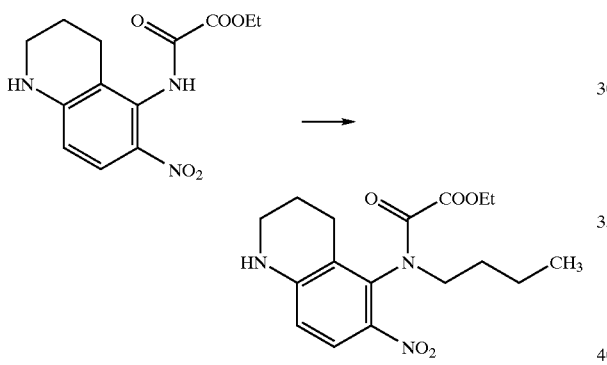

[Butyl(1,2,3,4-tetrahydro-6-nitro-5-quinolinyl)-
amino]oxo-acetic acid ethyl ester A mixture of the product form Example 87 (0.87 g, 3 mmol), bromobutane (0.49 g, 3.6 mmol) and cesium carbonate (1.17 g, 3.6 mmol) in 10 mL acetonitrile was stirred at room temperature for 4 hours. An additional equivalent of bromobutane and cesium carbonate was added and the reaction heated at 50° C. for 5 hours. Solids were removed by filtration and the filtrate concentrated. The residue was purified by silica gel chromatography (4:1 to 3:2 heptane:ethyl acetate as eluant) to give the title compound as a yellow syrup (0.63 g, 61% yield).

EXAMPLE 89

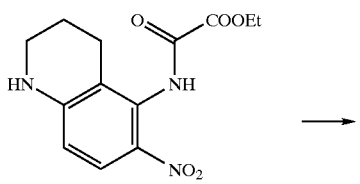

EXAMPLE 89 (continued)

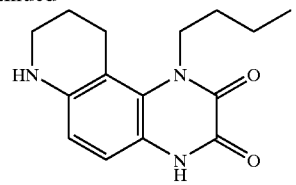

1-Butyl-1,4,7,8,9,10-hexahydropyrido-[3,2-f]
quinoxaline-2,3-dione

A solution of the product from Example 88 (0.63 g) in 75 mL of acetic acid was treated with 56 Pd/C (0.2 g) and shaken on a Parr apparatus under a hydrogen atmosphere (52 psi) for 12 hours. The catalyst was removed by filtration and the filtrate evaporated. The residue was washed with ether to give the title compound (0.35 g, 71% yield).

EXAMPLE 90

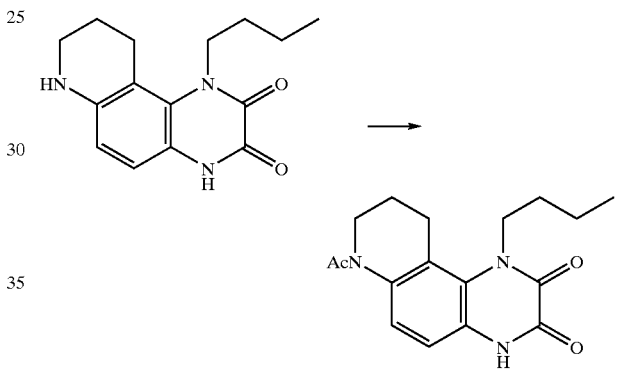

7-Acetyl-1-butyl-1,4,7,8,9,10-hexahydro-pyrido[3,2-
f]quinoxaline-2,3-dione

The product from Example 89 (0.14 g, 0.5 mmol) was solubilized in a minimal amount of dimethylformamide and then treated with 2 mL dichloromethane, acetic anhydride (0.15 g) and triethylamine (0.15 g). After the mixture stirred at room temperature for 18 h, it was poured onto dichloromethane/water. The aqueous layer was washed with dichloromethane and the combined organic layers over sodium sulfate, filtered and evaporated to give a dark syrup. The syrup was purified by silica gel chromatography (ethyl acetate as eluant) to give the title compound (30 mg, 19% yield).

EXAMPLE 91

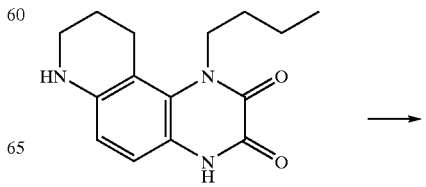

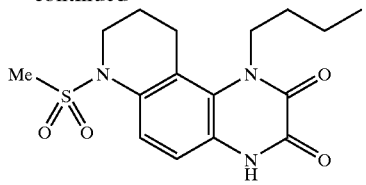

1-Butyl-1,4,7,8,9,10-hexahydro-7-methanesulfonyl-pyrido[3,2-f]quinoxaline-2,3-dione The product from Example 89 (0.12 g, 0.45 mmol) was solubilized in a minimal amount of dimethylformamide and then treated with 2 mL dichloromethane, methanesulfonyl chloride (0.17 g) and triethylamine (0.15 g). After stirring at room temperature for 4 h, the mixture was washed with water, dried over sodium sulfate, filtered and evaporated. The residue was purified by silica gel chromatography (4:1 heptane:ethyl acetate as eluant) to give the title compound (30 mg, 17% yield).

EXAMPLE 92

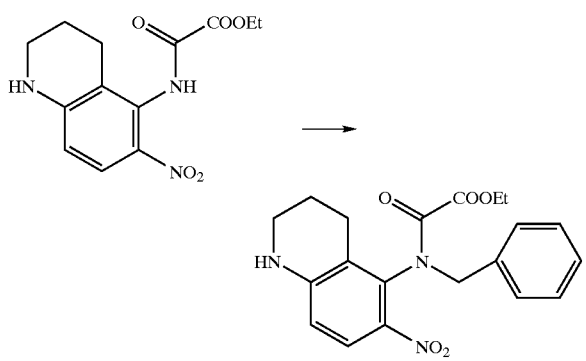

Oxo [(phenylmethyl)(1,2,3,4-tetrahydro-6-nitro-5-quinolinyl)amino]acetic acid ethyl ester A mixture of the product from Example 87 (0.58 g, 2 mmol), benzylbromide (0.41 g, 2.4 mmol) and cesium carbonate (0.78 g, 2.4 mmol) in 10 mL of acetonitrile was stirred at room temperature for 2 hours. The triethylamine hydrobromide was removed by filtration and the filtrate evaporated. The residue was purified by silica gel chromatography (2:1 heptane:ethyl acetate as eluant) to give the title compound as a yellow solid (0.7 g, 91% yield).

EXAMPLE 93

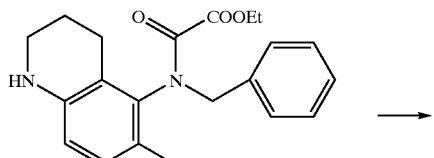

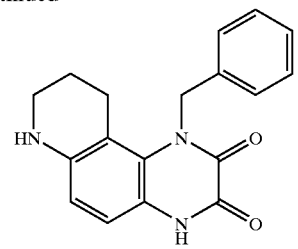

1,4,7,8,9,10-Hexahydro-(1-phenylmethyl)-pyrido-[3,2-f]quinoxaline-2,3-dione

A solution of the product from Example 92 (0.67 g, 1.7 mmol) in 20 ml tetrahydrofuran was treated with Raney nickel (0.1 g) and stirred under a hydrogen atmosphere (1 atm) for 48 hours. The Raney nickel was removed with a magnet and washed with methanol. The remaining solid was collected by filtration, washed with methanol and then dissolved in 2 N HCl and filtered. The filtrate was neutralized with saturated sodium bicarbonate and the precipitate collected by filtration and dried to give the title compound (0.30 g, 57% yield) mp>300° C.

Analysis for $C_{18}H_{16}N_3O_2 \cdot 0.6H_2O$: Calc: C, 67.95; H, 5.77; N, 13.21. Found: C, 67.68; H, 5.57; N, 13.11.

EXAMPLE 94

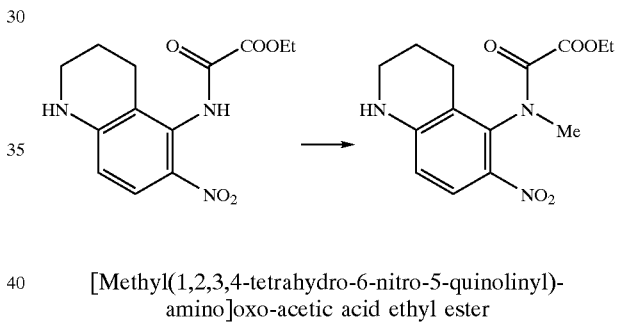

[Methyl(1,2,3,4-tetrahydro-6-nitro-5-quinolinyl)-amino]oxo-acetic acid ethyl ester A mixture of the product from Example 87 (0.87 g, 3 mmol), methyl iodide (0.51 g, 3.6 mmol) and cesium carbonate (1.17 g, 3.6 mmol) in 15 mL of acetonitrile was stirred at room temperature for 2 hours. The inorganic salts were removed by filtration and the filtrate evaporated. The residue was dissolved in methylene chloride, filtered and evaporated. The product was then used without further purification (0.86 g, 93% yield).

EXAMPLE 95

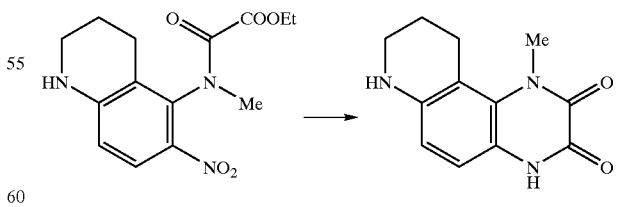

1,4,7,8,9,10-Hexahydro-1-methyl-pyrido-[3,2-f]-quinoxaline-2,3-dione

A solution of the product from Example 94 (1.1 g) in 100 mL of acetic acid was treated with 20% Pd/C (0.3 g) and shaken on a Parr apparatus under a hydrogen atmosphere (50

EXAMPLE 96

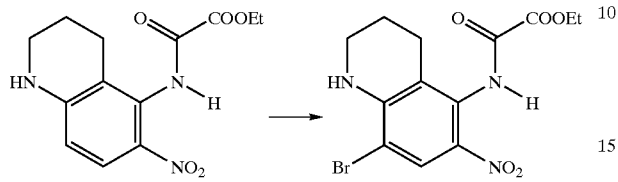

[(8-Bromo-1,2,3,4-tetrahydro-6-nitro-5-quinolinyl)-amino]oxo-acetic acid ethyl ester

A mixture of the product from Example 87 (0.15 g, 0.5 mmol) and N-bromosuccinimide (0.23 g, 1 mmol) in 2 mL dimethylformamide was stirred at room temperature for 18 hours. The solution was poured onto methylene chloride/water and separated and the water layer back extracted with methylene chloride. The combined organic layers were washed with water, dried over sodium sulfate, filtered and evaporated. The residue was purified by silica gel chromatography (4:1 to 1:1 heptane:ethyl acetate as eluant) to give the title compound (0.15 g, 81% yield).

EXAMPLE 97

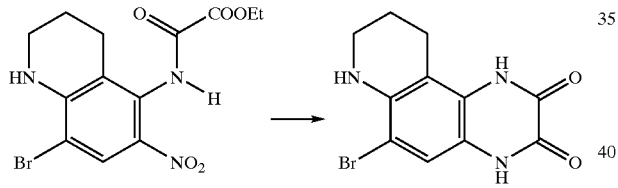

6-Bromo-1,4,7,8,9,10-hexahydro-pyrido[3,2-f]quinoxaline-2,3-dione

Raney nickel was washed with acetone (2×) and then with tetrahydrofuran (2×). A solution of the product from Example 96 (0.3 g, 0.8 mmol) in 30 mL tetrahydrofuran was added to the Raney nickel and was stirred at room temperature under a hydrogen atmosphere (1 atm) for 2 hours. The solution was decanted and filtered. The Raney nickel was washed with methanol and filtered and the combine filtrates were evaporated to give a yellow solid (0.1 g, 42% yield). HPLC analysis showed that 7% of the product was the debrominated quinoxalinedione.

EXAMPLE 98

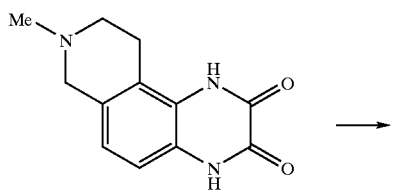

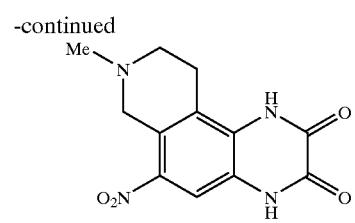

1,4,7,8,9,10-Hexahydro-8-methyl-6-nitro-pyrido-[4,3-f]quinoxaline-2,3-dione methansulfonate

A solution of the product from Example 22 (1.07 g,4.7 mmol) was dissolved in 20 ml sulfuric acid. Potassium nitrate (0.51 g, 5.0 mmol) was added in one portion, and the solution stirred for 1 hour. The solution was poured onto ice and made basic with ammonium hydroxide. The yellow solid which formed was filtered and washed with water and ether. The solid was purified by crystallization from water. The solid was suspended in water/DMF and 0.5 g methane sulphonic acid was added. The solution was concentrated, and the solid suspended in acetone, filtered and dried under vacuum (100° C.) to give the title compound (0.60 g, 35% yield), mp=292–294° C.

Analysis for $(C_{13}H_{15}N_3O_2.1.07\ CH_3SO_3H.0.9H_2O)$: Calc: C, 41.04; H, 4.39; N, 14.65; Cl, 8.97. Found: C, 41.02; H, 4.12; N, 14.25; Cl, 8.72.

EXAMPLE 99

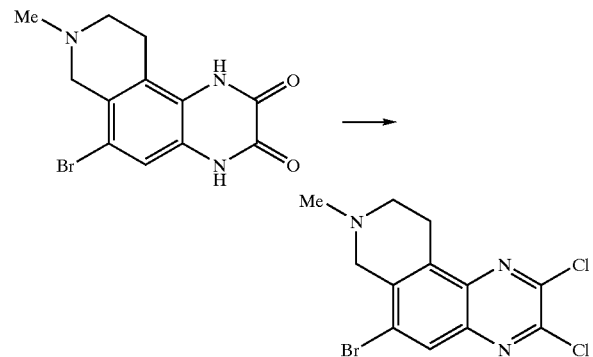

6-Bromo-2,3-dichloro-7,8,9,10-tetrahydro-8-methyl-pyrido[4,3-f]quinoxaline

A solution of the product from Example 19 (5.00 g, 14.4 mmol) was suspended in 200 mL thionyl chloride and dimethyl formamide (10.0 mL) was added. The resulting suspension was heated at reflux for 48 hours. The reaction mixture was cooled and concentrated. The residue was broken up in ether and collected by filtration to give the title compound as a yellow solid (5.44 g, 98% yield).

EXAMPLE 100

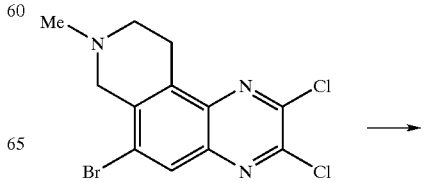

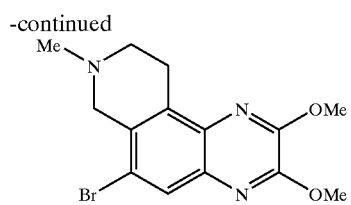

6-Bromo-7,8,9,10-tetrahydro-2,3-dimethoxy-8-methyl-pyrido[4,3-f]quinoxaline Sodium (2.85 g, 124 mmol) was dissolved in 200 mL of MeOH. The resulting solution was treated with the product from Example 99 (4.44 g, 11.6 mmol) and the resulting solution was stirred at room temperature for 18 hours. The reaction mixture was concentrated to approximately ½ volume and diluted with $CHCl_3$ (200 mL) and water (200 mL). The organic phase was collected and the aqueous phase was extracted with additional $CHCl_3$. The combined organic extracts were dried and concentrated. The residue was dissolved in hot acetonitrile, treated with activated charcoal and filtered. The solid which formed on cooling was collected and dried under vacuum to give the title compound as a white solid (2.12 g, 54% yield), mp=162° C.

Analysis for $C_{14}H_{16}BrN_3O_2$: Calc: C, 49.72; H, 4.77; N, 12.42. Found: C, 49.54; H, 4.73; N, 12.38.

EXAMPLE 101

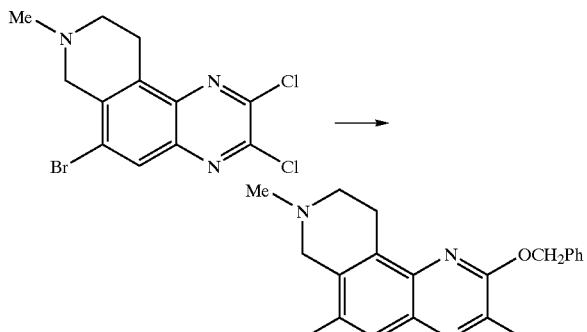

6-Bromo-7,8,9,10-tetrahydro-8-methyl-2,3-bis(phenylmethoxy)-pyrido[4,3-f]quinoxaline Sodium hydride (15.0 g, 375 mmol) was suspended in 500 mL of tetrahydrofuran and treated dropwise with benzyl alcohol (50 mL). When no further hydrogen evolution was observed the product from Example 99 (14.97 g, 39.0 mmol) was added in portions and the resulting solution stirred at room temperature for 48 hours. The reaction mixture was concentrated to approximately 100 mL volume and treated with $CH_2Cl_2$ (250 mL) and water (250 mL). The organic phase was collected and the aqueous phase was extracted with additional $CH_2Cl_2$ (4×200 mL). The combined organic extracts were dried and concentrated. The residue was placed under vacuum to remove the excess benzyl alcohol. The residue was purified by chromatography ($SiO_2$, 1:1 ethyl acetate, $CHCl_3$) to give a yellow solid. The solid was dissolved in hot acetonitrile, treated with charcoal and filtered. The solid which formed on cooling was collected by suction filtration and dried under vacuum to give the title compound as a yellow solid (7.16 g, 37% yield), mp=147° C.

Analysis for $C_{26}H_{24}BrN_3O_2$: Calc: C, 63.68; H, 4.93; N, 8.57. Found: C, 63.65; H, 4.92; N, 8.60.

EXAMPLE 102

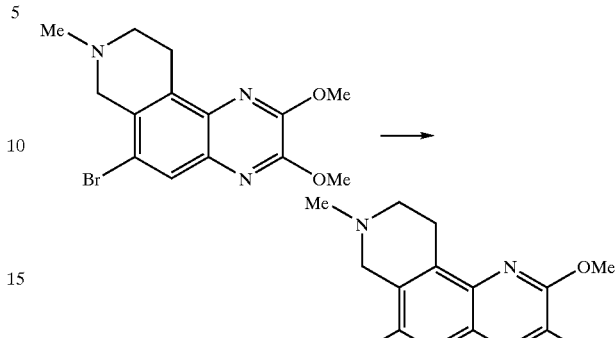

7,8,9,10-tetrahydro-2,3-dimethoxy-6,8-dimethyl-pyrido[4,3-f]quinoxaline

A solution of the product from Example 100 (0.50 g, 1.48 mol) in 20 mL of tetrahydrofuran was cooled to −78° C. and treated dropwise with sec-BuLi (1.7 mL, 1.17 M in cyclohexane). The resulting green-black solution was stirred at −78° C. for 30 minutes. The reaction mixture was treated with MeI (123 µL, 2.00 mmol) and the resulting solution stirred at −78° C. for 30 minutes. The reaction mixture was warmed to room temperature and quenched with saturated aqueous $NH_4Cl$ solution (2.0 mL). The reaction mixture was extracted with $CHCl_3$ (4×20 mL) and the combined organic extracts were dried and concentrated. The residue was broken up in heptane and collected by suction filtration to give the title compound as a orange solid (0.196 g, 48% yield).

EXAMPLE 103

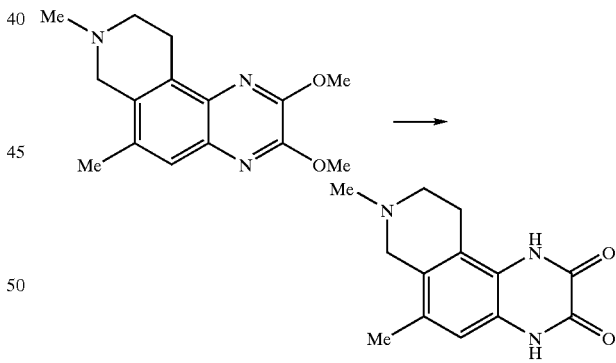

1,4,7,8,9,10-Hexahydro-6,8-dimethyl-pyrido-[4,3-f]quinoxaline-2,3-dione Hydrochloride A solution of the product from Example 102 (0.172 g, 0.63 mmol) in 4 mL of aqueous 3N HCl solution was heated at reflux for 2 hours. The hot solution was treated with charcoal and filtered. The filtrate was cooled to 5° C. and the solid which formed was collected by filtration and dried at 90° C. under vacuum to give the title compound as a white solid (83 mg, 43% yield), mp=323–330° C.

Analysis for ($C_{13}H_{15}N_3O_2 \cdot HCl \cdot 1.25 H_2O$): Calc: C, 51.32; H, 6.13; N, 13.81; Cl, 11.65. Found: C, 51.41; H, 5.88; N, 13.58; Cl, 11.62.

EXAMPLE 104

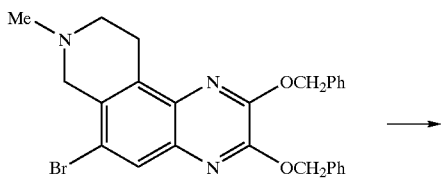

7,8,9,10-Tetrahydro-8-methyl-2,3-bis(phenylmethoxy)-pyrido[4,3-f]quinoxaline carboxylic acid methyl ester A suspension of the product from Example 100 (2.40 g, 5.19 mmol) was placed in a pressure reactor and acetonitrile (75 mL), methanol (5.0 g), triethylamine (1.5 g), and bis(triphenylphosphine)-palladium dichloride (0.5 g) was added. The reactor was sealed and charged to 820 psi with carbon monoxide and heated to 100° C. for 63 hours. The reaction vessel was cooled to room temperature and the contents dissolved in $CHCl_3$ and washed with saturated aqueous $NaHCO_3$ solution. The organic phase was separated and the aqueous phase washed with additional $CHCl_3$. The combined organic extracts were dried and concentrated. The residue was suspended in acetonitrile and collected by filtration. The solid was dried under vacuum to give the title compound as a yellow solid (1.17 g, 48% yield) mp=167–168° C.

EXAMPLE 105

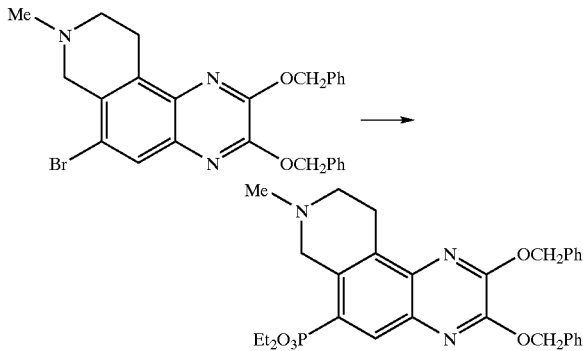

7,8,9,10-Tetrahydro-8-methyl-2,3-bis(phenylmethoxy)-pyrido[4,3-f]quinoxalin-6-yl phosphonic acid diethyl ester A solution of the product from Example 100 (1.83 g, 3.73 mmol) was dissolved in dry toluene and treated with diethylphosphite (0.72 mL, 5.59 mmol), triethylamine (1.56 mL, 11.2 mmol) and tetrakis (triphenylphosphine)palladium (0) (0.44 g, 0.37 mmol). The resulting solution was heated to reflux under a nitrogen atmosphere for 48 hours. The reaction mixture was concentrated and the residue was dissolved in $CHCl_3$ and washed with saturated aqueous $NaHCO_3$ solution. The organic phase was dried, filtered and concentrated. The residue was purified by chromatography ($SiO_2$, gradient elution EtOAc then 5:1 EtOAc/EtOH). The material obtained was dissolved in hot $iPr_2O$, filtered and concentrated. The residue was then broken up in a mall amount of $iPr_2O$ and the solid collected by filtration and dried under vacuum to give the title compound as a yellow solid (0.74 g, 36% yield), mp=104° C. The filtrates were concentrated to give an additional 0.77 g of the title compound.

Analysis for $C_{30}H_{34}N_3O_5P$: Calc: C, 65.80; H, 6.26; N, 7.27. Found: C, 65.38; H, 6.33; N, 7.62.

EXAMPLE 106

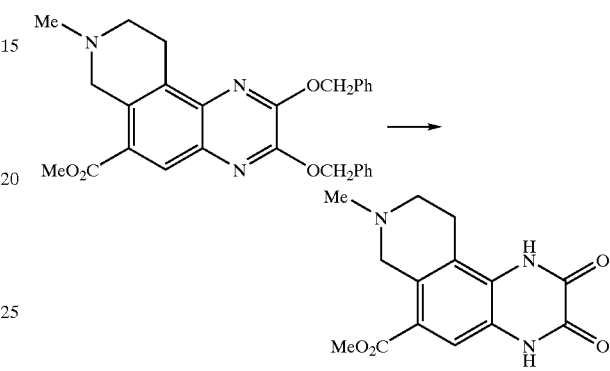

1,2,3,4,8,9,10-Octahydro-8-methyl-2,3-dioxopyrido[4,3-f]quinoxaline-6-carboxylic acid methyl ester A solution of the product from Example 104 (0.10 g, 0.21 mmol) in 75 mL acetic acid was hydrogenated at 52 psi over 20% Pd/C (0.1 g). The reaction mixture was filtered and concentrated. The residue was broken up in ether and collected by filtration to give the title compound as a white solid (42 mg, 69% yield), mp=290–300° C. (dec.).

EXAMPLE 107

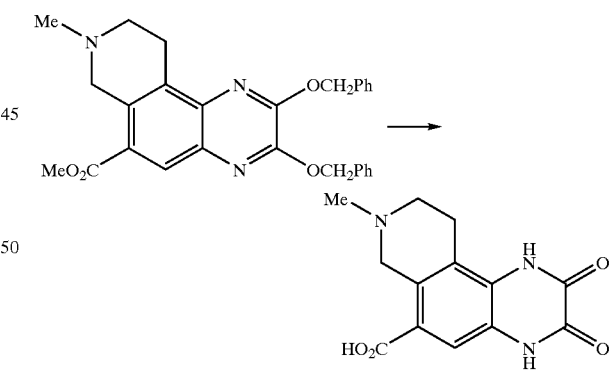

1,2,3,4,8,9,10-Octahydro-8-methyl-2,3-dioxopyrido-[4,3-f]quinoxaline-6-carboxylic acid hydrochloride A suspension of the product from Example 104 (0.20 g, 0.73 mmol) in 5 mL of aqueous 3N HCl solution was heated at reflux for 24 hours. The reaction mixture was cooled and the solid collected by filtration. The solid obtained was crystallized from hot water and collected. The solid was dissolved in aqueous 1N NaOH (1.0 mL) and stirred for 24 hours at room temperature. The reaction was treated with 0.5 mL aqueous 3N HCl and the solid which formed was collected by filtration, washed with cold water and dried under vacuum to give the title compound as a white solid (51 mg) mp>325° C.

Analysis for $C_{13}H_{13}N_3O_4 \cdot HCl$: Calc: C, 50.09; H, 4.53; N, 13.48. Found: C, 49.50; H, 4.72; N, 13.31.

EXAMPLE 108

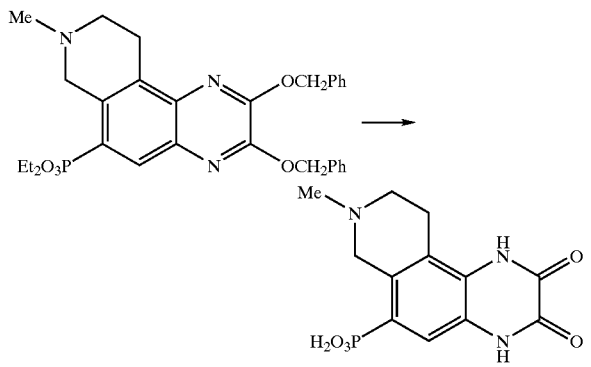

1,2,3,4,7,8,9,10-Octahydro-8-methyl-2,3-dioxopyrido[4,3-f]quinoxalin-6-yl phosphonic acid A solution of the product form Example 105 (0.70 g, 1.28 mmol) in 30 mL of aqueous 6N HCl was heated at reflux for 24 hours. The reaction mixture was cooled to room temperature and washed with ether. The aqueous phase was heated to 50° C. and treated with charcoal, filtered and concentrated. The residue was crystallized from hot water. The solid which formed was collected by filtration and dried under vacuum to give the title compound as a tan solid (56 mg) mp >325° C.

EXAMPLE 109

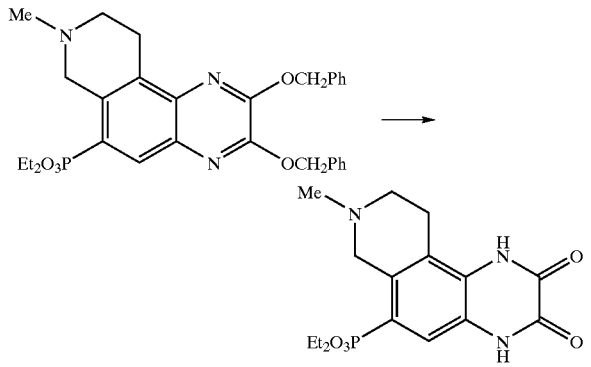

1,2,3,4,7,8,9,10-Octahydro-8-methyl-2,3-dioxopyrido[4,3-f]quinoxalin-6-yl phoshonic acid diethyl ester A solution of the compound from Example 105 (0.34 g, 0.65 mmol) was dissolved in 60 mL of acetic acid and hydrogenated at 52 psi over 20% Pd/C. The reaction mixture was filtered and concentrated. The residue was dissolved in EtOH (3 mL) and concentrated. This procedure was repeated several times. The residue was then dissolved in EtOH and triturated with ethyl acetate. The solid which formed was collected by suction filtration and dried under vacuum to give the title compound as a yellow solid (0.20 g, 83% yield) mp 310–330° C. (dec).

EXAMPLE 110

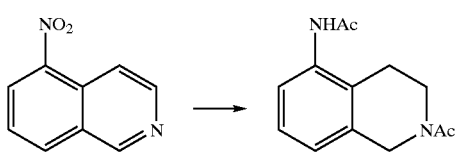

N-(2-acetyl-1,2,3,4-tetrahydro-5-isoquinolinyl)-acetamide

A solution of 5-nitroisoquinoline (44.8 g, 0.257 mol) in 600 mL of acetic acid and 50 mL acetic anhydride was hydrogenated at 62 psi over $PtO_2$ (0.5 g). The reaction mixture was filtered and concentrated. The residue was purified by chromatography ($SiO_2$, 10:1 EtOAc/EtOH) to give the title compound as a white solid (11.25 g, 19% yield). An analytical was obtained by crystallization from THF/$iPr_2O$, mp=154–156° C.

EXAMPLE 111

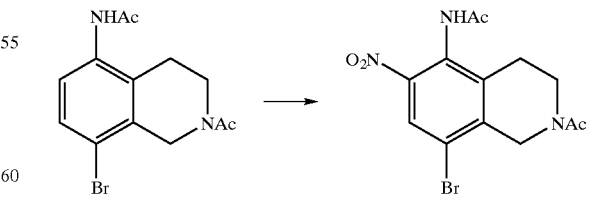

N-(2-acetyl-8-bromo-1,2,3,4-tetrahydro-5-isoquinolinyl)acetamide

A solution of the product from Example 110 (6.67 g, 28.7 mmol) in triflouroacetic acid (200 mL) was treated with 30 mL of a 1M solution of bromine in acetic acid and the resulting solution was stirred at room temperature for 24 hours. The reaction mixture was concentrated and the residue was partitioned between $CHCl_3$ and saturated aqueous $NaHCO_3$. The organic phase was collected, dried over $K_2CO_3$, filtered and concentrated. The residue was flushed through a plug of silica gel eluting with 4.5:4.5:1 EtOAc/EtOH/$NH_4OH$ and concentrated to give the give the title compound as a pale pink solid (3.00 g, 34% yield). An analytical was obtained by crystallization from THF/$iPr_2O$, mp=192–193° C.

Analysis for $C_{13}H_{15}BrN_2O_2$: Calc: C, 50.18; H, 4.86; N, 9.00. Found: C, 50.29; H, 4.99; N, 8.83.

EXAMPLE 112

N-(2-acetyl-8-bromo-1,2,3,4-tetrahydro-6-nitro-5-isoquinolinyl)acetamide

A solution of the product from Example 111 (1.00 g, 3.21 mmol) in 20 mL of triflouroacetic acid was treated with 4 mL of fuming nitric acid dropwise with stirring. The resulting solution was stirred at room temperature for 24 hours. The reaction mixture was concentrated and the residue was dissolved in CHCl₃ and washed with saturated aqueous NaHCO₃ solution. The organic phase was dried and concentrated to give the title compound as a tan solid (0.774 g, 68% yield). An analytical was obtained by crystallization from ethyl acetate, mp=171° C.

Analysis for $C_{13}H_{14}BrN_3O_4$: Calc: C, 43.83; H, 3.96; N, 11.79. Found: C, 43.96; H, 3.96; N, 11.91.

EXAMPLE 113

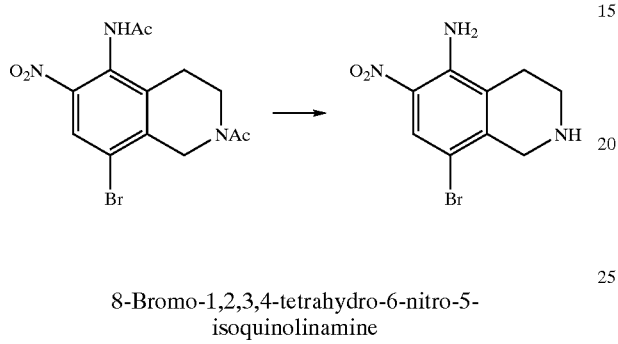

8-Bromo-1,2,3,4-tetrahydro-6-nitro-5-isoquinolinamine

A solution of the product from Example 112 is heated in aqueous 3N HCl until no starting material remains. The reaction mixture is concentrated to give the title compound.

EXAMPLE 114

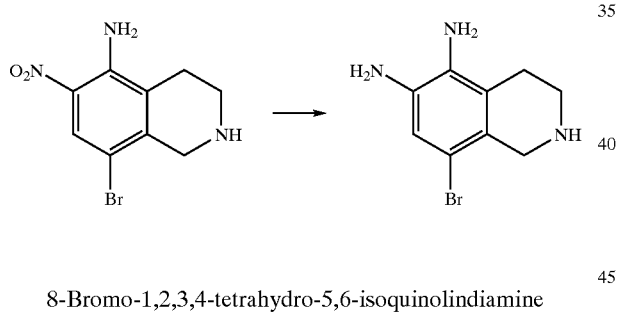

8-Bromo-1,2,3,4-tetrahydro-5,6-isoquinolindiamine

The product from Example 113 is converted to the title compound by the procedure described in Example 13.

EXAMPLE 115

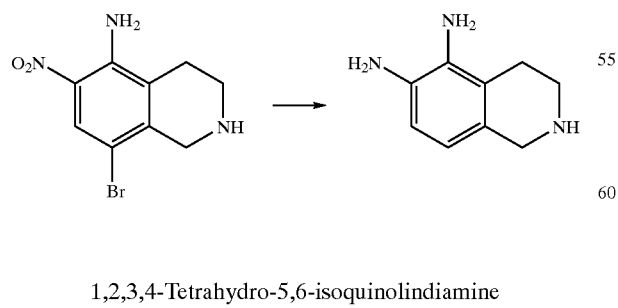

1,2,3,4-Tetrahydro-5,6-isoquinolindiamine

The product from Example 113 is converted to the title compound by the procedure described in Example 16.

EXAMPLE 116

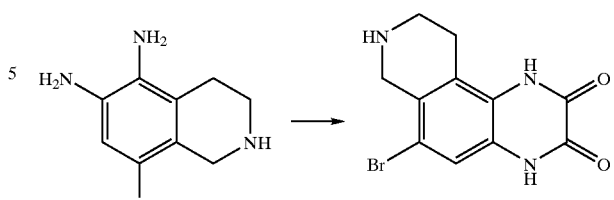

6-Bromo-1,4,7,8,9,10-hexahydropyrido[4,3-f]quinoxaline-2,3-dione

The product from Example 114 is converted to the title compound by the procedure described in Example 19.

EXAMPLE 117

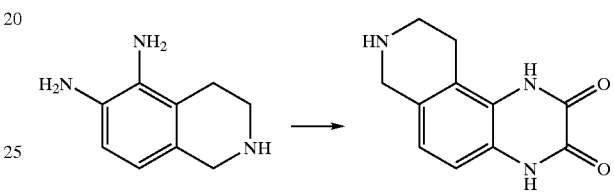

1,4,7,8,9,10-Hexahydropyrido[4,3-f]quinoxaline-2,3-dione

The product from Example 115 is converted to the title compound by the procedure described in Example 19.

EXAMPLE 118

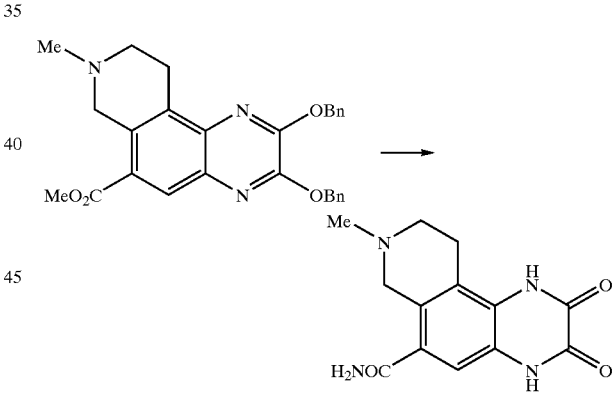

1,2,3,4,7,8,9,10-Octahydro-8-methyl-2,3-dioxopyrido[4,3-f]quinoxalin-6-carboxamide The product from Example 104 is dissolved in toluene and treated dropwise with a solution of trimethylaluminum and ammonium hydrochloride in toluene. The product obtained is hydrolyzed in 3N HCl solution to give the title compound.

In a similar manner are prepared:
1,2,3,4,7,8,9,10-Octahydro-N,N,8-trimethyl-2,3-dioxopyrido[4,3-f]quinoxalin-6-carboxamide;
1-[(1,2,3,4,7,8,9,10-Octahydro-8-methyl-2,3-dioxopyrido[4,3-f]quinoxalin-6-yl carbonyl pyrrolidine;
1,2,3,4,7,8,9,10-Octahydro-9-methyl-2,3-dioxopyrido[3,4-f]quinoxalin-6-carboxamide;

1,2,3,4,7,8,9,10-Octahydro-N,N,9-trimethyl-2,3-dioxopyrido[3,4-f]quinoxalin-6-carboxamide; and 1-[(1,2,3,4,7,8,9,10-Octahydro-9-methyl-2,3-dioxopyrido[3,4-f]quinoxalin-6-yl carbonyl pyrrolidine.

EXAMPLE 119

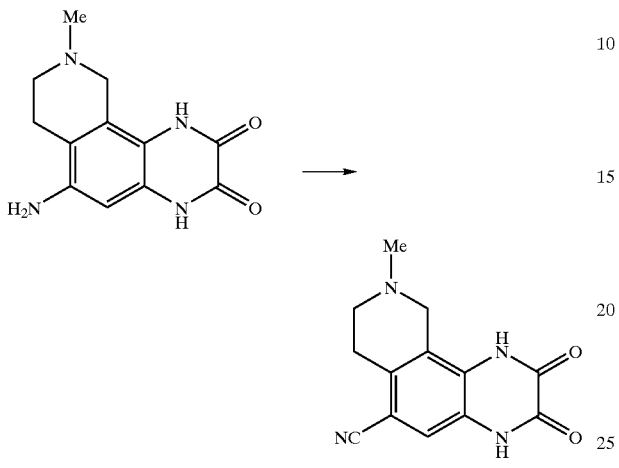

1,2,3,4,7,8,9,10-Octahydro-9-methyl-2,3-dioxopyrido[3,4-f]quinoxaline-6-carbonitrile The product from Example 79 is treated with sodium nitrite in 37% HCl solution at 0° C. The reaction mixture is poured into a solution of CuCN and the title compound is isolated by filtration.

In a similar manner is prepared:

1,2,3,4,7,8,9,10-Octahydro-8-methyl-2,3-dioxopyrido[4,3-f]quinoxaline-6-carbonitrile.

What is claimed is:

1. A compound having the formula

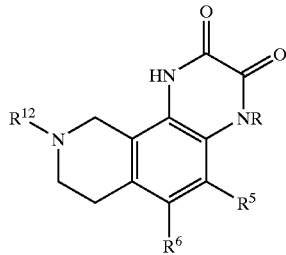

wherein

R is hydrogen or hydroxy;

$R^{12}$ is hydrogen $CH_2CH_2OH$, or alkyl; and $R^5$ and $R^6$ are each independently hydrogen, halogen, $NO_2$, CN, $CF_3$, and/or $SO_2NR^7R^8$, wherein $R^7$ and $R^8$ are each independently hydrogen or alkyl.

2. A compound according to claim 1 of formula

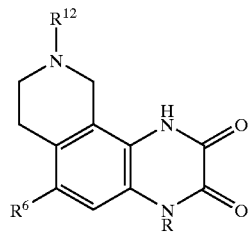

wherein

R is hydrogen;

$R^{12}$ is hydrogen, methyl, or ethyl; and $R^6$ is $NO_2$, or $SO_2NMe_2$.

3. A pharmaceutical composition comprising a therapeutically effective amount of the compound of claim 1 together with a pharmaceutically acceptable carrier.

4. A compound according to claim 1 named 1,4,7,8,9,10-hexahydro-9-methyl-pyrido[3,4-f]quinoxaline-2,3-dione;

9-ethyl-1,4,7,8,9,10-hexahydro-pyrido[3,4-f]quinoxaline-2,3-dione;

6-bromo-9ethyl-1,4,7,8,9,10-hexahydro-pyrido[3,4-f]quinoxaline-2,3-dione;

6-bromo-1,4,7,8,9,10-hexahydro-9-methyl-pyrido[3,4-f]quinoxaline-2,3-dione;

1,2,3,4,7,8,9,10-octahydro-N,N,9-trimethyl-2,3-dioxo-pyrido[3,4-f]quinoxaline-6-sulfonamide;

1,2,3,4,7,8,9,10-octahydro-9-methyl-2,3-dioxo-pyrido[3,4-f]quinoxaline-6-sulfonamide;

9-ethyl-1,2,3,4,7,8,9,10-octahydro-N,N-dimethyl-2,3-dioxo-pyrido[3,4-f]quinoxaline-6-sulfonamide;

9-Ethyl-1,4,7,8,9,10-hexahydro-6nitro-pyrido[3,4-f]quinoxaline-2,3-dione;

9-Ethyl-1,4,7,8,9,10-hexahydro-6nitro-pyrido[3,4-f]quinoxaline-2,3-dione; methanesulfonate;

6-Bromo-1,4,7,8,9,10-hexahydro-9-methyl-pyrido[3,4-f]quinoxaline-2,3-dione; methansulfonate;

1,4,7,8,9,10-Hexahydro-9-methyl-pyrido[3,4-f]quinoxaline-2,3-dione; monohydrochloride;

1,4,7,8,9,10-Hexahydro-9-methyl-6-nitro-pyrido[3,4-f]quinoxaline-2,3-dione; methansulfonate; or 1,2,3,4,7,8,9,10-Octahydro-9-methyl-2,3-dioxo-pyrido[3,4-f]quinoxaline-6-carbonitrile.

* * * * *